US011667900B2

(12) United States Patent
Wang et al.

(10) Patent No.: US 11,667,900 B2
(45) Date of Patent: Jun. 6, 2023

(54) COMPOSITIONS AND METHODS FOR ENHANCING MACROPHAGE-MEDIATED ANTIBODY GUIDED CANCER CELL OR TUMOR ERADICATION

(71) Applicant: The Regents of the University of California, Oakland, CA (US)

(72) Inventors: Yingxiao Wang, San Diego, CA (US); Shu Chien, La Jolla, CA (US); Lei Lei, San Diego, CA (US); Shaoying Lu, San Diego, CA (US); Jie Sun, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 380 days.

(21) Appl. No.: 16/631,041

(22) PCT Filed: Jul. 12, 2018

(86) PCT No.: PCT/US2018/041766
§ 371 (c)(1),
(2) Date: Jan. 14, 2020

(87) PCT Pub. No.: WO2019/014419
PCT Pub. Date: Jan. 17, 2019

(65) Prior Publication Data
US 2020/0140834 A1    May 7, 2020

Related U.S. Application Data

(60) Provisional application No. 62/532,661, filed on Jul. 14, 2017.

(51) Int. Cl.
*C12N 9/16* (2006.01)
*A61K 38/00* (2006.01)
*A61K 39/395* (2006.01)
*C07K 14/435* (2006.01)

(52) U.S. Cl.
CPC .......... *C12N 9/16* (2013.01); *A61K 39/39558* (2013.01); *C07K 14/435* (2013.01); *C12Y 301/03048* (2013.01); *A61K 38/00* (2013.01); *C07K 2319/03* (2013.01); *C07K 2319/61* (2013.01)

(58) Field of Classification Search
CPC .............. A61K 38/00; A61K 39/39558; C07K 2319/03; C07K 14/435; C07K 2319/61; C12N 9/16; C12Y 301/03048
See application file for complete search history.

(56) References Cited

U.S. PATENT DOCUMENTS

| | | |
|---|---|---|
| 6,156,551 A | 12/2000 | Neel et al. |
| 2005/0026234 A1 | 2/2005 | Violin et al. |
| 2010/0239579 A1* | 9/2010 | Smith ............ A61P 37/00 424/134.1 |
| 2011/0165602 A1 | 7/2011 | Zhang et al. |

FOREIGN PATENT DOCUMENTS

WO    2017087912 A2    5/2017

OTHER PUBLICATIONS

Ohnishi et al, Differential Localization of Src Homology 2 Domain-Containing Protein Tyrosine Phosphatase Substrate-1 and CD47 and its Molecular Mechanisms in Cultured Hippocampal Neurons, Journal of Neuroscience, 2005, 25(10), pp. 2702-2711 (Year: 2005).*
Xiang et al., "A FRET-Based biosensor for imaging SYK activities in living cells" Cell mol Bioeng., 2011, v 4, n 4, p. 670-677.
Sun et al., "Antagonism between binding site affinity and conformational dynamics tunes alternative cis-interactions within Shp2" Nature Communications, 2013, p. 1-11.

* cited by examiner

*Primary Examiner* — Mark Halvorson
*Assistant Examiner* — Dennis J Sullivan
(74) *Attorney, Agent, or Firm* — Greer, Burns & Crain, Ltd.; Gregory P. Einhorn

(57) ABSTRACT

Provided are Shp2- and Spleen tyrosine kinase (Syk)-integrated sensing and actuating protein (iSNAP) (Shp2- and Syk-iSNAP) chimeric proteins comprising: a bi-phosphorylatable peptide, optionally a bisphosphoryl tyrosine-based activation (BTAM) motif; a Fluorescent Protein (FP) Förster Resonance Energy Transfer (FRET) (or FP FRET) pair or pair of motifs; a truncated Shp2 domain comprising an N-Src Homology 2(N-SH2) domain and a C-Src Homology 2(C-SH2) domain; and, a phosphatase (PTP) domain or a kinase domain. Provided are engineered cells and methods for cancer cell or tumor eradication, or for the treatment or amelioration of a cancer, tumor or dysfunctional cell, or for promoting an anti-cancer, anti-tumor or anti-dysfunctional cell inflammatory response, including enhancing macrophage-, monocyte-, microglia-, osteoclast-, Kupffer cell- or dendritic cell-mediated antibody- or monoclonal antibody (mAb)-guided cancer or dysfunctional cell or tumor eradication, amelioration, or treatment.

23 Claims, 8 Drawing Sheets

US 11,667,900 B2

COMPOSITIONS AND METHODS FOR ENHANCING MACROPHAGE-MEDIATED ANTIBODY GUIDED CANCER CELL OR TUMOR ERADICATION

RELATED APPLICATIONS

This application is a national phase application claiming benefit of priority under 35 U.S.C. § 371 to Patent Convention Treaty (PCT) International Application serial number PCT/US2018/041766, filed Jul. 12, 2018, which claims the benefit of priority to U.S. Provisional Application Ser. No. 62/532,661 filed Jul. 14, 2017. The aforementioned applications are expressly incorporated herein by reference in their entirety and for all purposes.

This invention was made with government support HL098472, HL109142, and HL121365 awarded by the National Institutes of Health and under CBET1360341, DMS1361421, and NSFC 11428207 awarded by the National Science Foundation. The government has certain rights in the invention.

TECHNICAL FIELD

This invention generally relates to cell biology, cellular genetic engineering and directed cancer immunotherapeutics. In alternative embodiments, provided is a Shp2- and Spleen tyrosine kinase (Syk)-integrated sensing and actuating protein (iSNAP) (Shp2- and Syk-iSNAP) chimeric protein comprising: a bi-phosphorylatable peptide, optionally a bisphosphoryl tyrosine-based activation (BTAM) motif; a Fluorescent Protein (FP) Förster Resonance Energy Transfer (FRET) (or FP FRET) pair or pair of motifs, optionally an enhanced cyan fluorescent protein (ECFP) motif and a YPet fluorochrome; a truncated Shp2 domain comprising an N-Src Homology 2 (N-SH2) domain and a C-Src Homology 2 (C-SH2) domain; and, a phosphatase (PTP) domain or a kinase domain. Also provided are engineered cells and methods for cancer cell or tumor eradication, or for the treatment or amelioration of a cancer, tumor or dysfunctional cell, or for promoting an anti-cancer, anti-tumor or anti-dysfunctional cell inflammatory response, including enhancing macrophage-, monocyte-, dendritic cell-, microglia-, osteoclast- or Kupffer cell-mediated antibody- or monoclonal antibody (mAb)-guided cancer or dysfunctional cell or tumor eradication, amelioration, or treatment.

BACKGROUND

Immunotherapy has emerged as a promising novel direction for cancer therapeutics. Monoclonal antibody (mAb) therapies directly targeting cancer cells have also been widely used. Macrophages play a prominent role in mAb-based cancer immunotherapy by phagocytosis of tumor cells (Weiskopf and Weissman 2015). Macrophage phagocytosis results from a balance between the pro-phagocytic ("eat me") and anti-phagocytic ("don't eat me") signals. Antigen-targeting antibody can ligate FcγRs on macrophages and trigger pro-phagocytic signaling, while the anti-phagocytic signaling is mediated by CD47 (also known as integrin associated protein (IAP)) on the target cell engaging the corresponding receptor SIRPα on macrophages (Barclay and Van den Berg 2014). In fact, anti-CD47 antibody has been applied to prevent anti-phagocytic signaling and to promote tumor eradication in various cancer types (Chao, Alizadeh et al. 2010; Jaiswal, Chao et al. 2010; Tseng, Volkmer et al. 2013). CD47 is, however, also expressed at high levels in red blood cells (RBCs), and undesirable anemia may complicate anti-CD47 cancer therapy (Barros, Yamamoto et al. 2009; Liu, Wang et al. 2015).

Current monoclonal antibody (mAb) mediated cancer immunotherapy is now one of the most successful and important strategies, however its efficacy is compromised by the "don't eat me" signal CD47 highly expressed on cancer cells (Weiskopf and Weissman 2015). Developing anti-CD47 cancer therapy utilizing antibodies shows high potential for cancer immunotherapy, however undesirable anemia may complicate this approach (Barros, Yamamoto et al. 2009; Liu, Wang et al. 2015).

SUMMARY

In alternative embodiments, provided is a Src homology region 2 domain-containing phosphatase-2 (Shp2)- and Spleen tyrosine kinase (Syk)-integrated sensing and actuating protein (iSNAP) (Shp2- and Syk-iSNAP, or Shp2-iSNAP) chimeric protein comprising:

(a) a phosphorylatable peptide, optionally a bi-phosphorylatable peptide, wherein optionally the bi-phosphorylatable peptide comprises a bisphosphoryl tyrosine-based activation (BTAM) motif, (b) a Fluorescent Protein (FP) Förster Resonance Energy Transfer (FRET) (FP FRET) pair or pair of motifs, wherein optionally the FP FRET pair or pair of motifs is or comprises an enhanced cyan fluorescent protein (ECFP) motif and a YPet fluorochrome, (c) a truncated Shp2 domain comprising an N-Src Homology 2 (N-SH2) domain and a C-Src Homology 2 (C-SH2) domain; and, (d) a phosphatase (PTP) domain or a kinase domain, wherein optionally the kinase comprises a tyrosine kinase (Syk), wherein the unphosphorylated N-SH2 domain binds or quenches the PTP domain or the kinase domain, and when phosphorylated (or bi-phosphorylated), the phosphorylated (or bi-phosphorylatable) peptide or BTAM motif binds the N-SH2 domain and the C-SH2 domain and liberates or unquenches (activates) the PTP domain or the kinase domain, and unquenching or activating of the PTP domain or the kinase domain causes (or results in the) emission of a detectable signal by the FP FRET pair or pair of motifs, and optionally, if the FP FRET pair or pair of motifs is or comprises an enhanced cyan fluorescent protein (ECFP) motif and a YPet fluorochrome, when the YPet fluorochrome comes into physical proximity to the enhanced cyan fluorescent protein (ECFP) motif, the physical proximity causes the YPet fluorochrome to emit a 535 nm signal.

In alternative embodiments, the Shp2-iSNAP chimeric protein as provided herein further comprises:

(a) a transmembrane domain;

(b) an extracellular domain capable of binding to a ligand; or (c) a transmembrane domain and an extracellular domain capable of binding to a ligand, wherein optionally the transmembrane domain is joined or fused to the phosphorylatable peptide, or bi-phosphorylatable peptide or BTAM motif, and when the extracellular domain binds to its ligand the phosphorylatable peptide are phosphorylated (or the bi-phosphorylatable peptide or BTAM motif are biphosphorylated), and when phosphorylated (or bi-phosphorylated), the phosphorylated (or bi-phosphorylated peptide or BTAM motif) binds the N-SH2 domain and the C-SH2 domain and liberates or unquenches (activates) the PTP domain or the kinase domain, and the unquenching or activating of the PTP domain or the kinase domain causes emission of a detectable signal by the FP FRET pair or pair of motifs, and optionally, if the FP FRET pair or pair of motifs is or comprises an enhanced cyan fluorescent protein (ECFP) motif and a YPet fluorochrome, the YPet fluorochrome comes into physical proximity to the enhanced cyan fluorescent protein (ECFP) motif, thereby causing the YPet fluorochrome to emit a 535 nm signal, wherein optionally the extracellular domain capable of binding to a ligand comprises a Signal Regulatory Protein α (SIRPα), or a human SIRPα, domain and the ligand comprises a Cluster of Differentiation 47 (CD47) protein, optionally a CD47-coated particle or a CD47-expressing liposome or cell.

In alternative embodiments, provided are recombinant nucleic acids encoding a Shp2-iSNAP chimeric protein as provided herein.

In alternative embodiments, provided are expression vehicles or cassettes, vectors, viruses (e.g., recombinant viruses), and plasmids comprising or having contained therein a nucleic acid as provided herein, wherein optionally the virus is or is derived from a lentivirus, a poliovirus, or an adenovirus.

In alternative embodiments, provided are engineered (or recombinant) cells comprising or having contained therein a nucleic acid as provided herein, or an expression vehicle or cassette, vector or plasmid as provided herein, wherein optionally the cell is a bacterial cell, a yeast cell, a mammalian cell or a human cell, and optionally the cell is a macrophage, a microglial cell, an osteoclast, a Kupffer cell or a monocyte.

In alternative embodiments, provided are engineered eukaryotic cells comprising or expressing a Shp2-iSAP chimeric protein as provided herein, or comprising or having contained therein a nucleic acid as provided herein, or an expression vehicle or cassette, vector or plasmid as provided herein, wherein optionally the cell is a mammalian cell or a human cell, or an immune cell, or a macrophage, a monocyte, a microglial cell, an osteoclast, a Kupffer cell or a dendritic cell, wherein optionally the immune cell, or the macrophage, monocyte, microglial cell, osteoclast, Kupffer cell or dendritic cell is a human macrophage, microglial cell, osteoclast, Kupffer cell monocyte or dendritic cell.

In alternative embodiments, provided are methods for:
enhancing a macrophage-, monocyte-, microglia-, osteoclast- or Kupffer cell- or dendritic cell-mediated antibody (Ab)- or monoclonal antibody (mAb)-guided cancer cell, dysfunctional cell or tumor treatment or eradication,
promoting development of an M1 macrophage phenotype,
treating or ameliorating a cancer, a tumor or a condition caused by a dysfunctional cell, or
for enhancing or initiating a macrophage-, monocyte-, microglia-, osteoclast- or Kupffer cell- or dendritic cell-mediated anti-cancer, anti-tumor or anti-dysfunctional cell inflammatory response,
the method comprising:
(a) providing or having provided an engineered macrophage, monocyte, microglial cell, osteoclast, Kupffer cell or dendritic cell as provided herein, wherein the macrophage, monocyte, microglial cell, osteoclast, Kupffer cell or dendritic cell expresses a Shp2-iSNAP chimeric protein comprising a transmembrane domain and an extracellular domain capable of binding to a ligand (wherein optionally the ligand is a CD47 ligand) expressed on the cancer or dysfunctional cell or tumor, wherein the transmembrane domain is joined or fused to the phosphorylatable peptide (optionally a bi-phosphorylatable peptide or BTAM motif), and when the extracellular domain binds to its ligand (optionally a CD47 ligand) the phosphorylatable peptide is phosphorylated (or the bi-phosphorylatable peptide or BTAM motif are biphosphorylated), and when phosphorylated (or bi-phosphorylated), the phosphorylated (or bi-phosphorylated peptide or BTAM motif) binds the N-SH2 domain and the C-SH2 domain and liberates or unquenches (activates) the PTP domain or the kinase domain, and the unquenching or activating of the PTP domain or the kinase domain causes emission of a detectable signal by the FP FRET pair or pair of motifs, and optionally, if the FP FRET pair or pair of motifs is or comprises an enhanced cyan fluorescent protein (ECFP) motif and a YPet fluorochrome, the YPet fluorochrome comes into physical proximity to the enhanced cyan fluorescent protein (ECFP) motif, thereby causing the YPet fluorochrome to emit a 535 nm signal, and liberating or unquenching (activating) the PTP domain or the kinase domain bypassing a CD47 mediated phagocytosis-block signal, wherein optionally the fusion of Shp2-iSNAP to the C-tail of SIRPα (SIRPα Shp2- or Syk-iSNAP) rewires the anti-phagocytic "don't eat me" CD47/SIRPα/Shp1 negative signaling (the native CD47-SIRPα pathway in myeloid cells is mediated by the negative regulator Shp1) into a positive Shp2 or Syk action upon the engagement of CD47 (or binding of the extracellular domain to its ligand CD47), thus facilitating phagocytosis of opsonized tumor cells, wherein the opsonization is initiated by IgG-FcγR interactions;

(b) providing or having provided an anti-tumor, anti-cancer or anti-dysfunctional cell Fc domain-comprising antibody or mAb capable of specifically binding to the cancer or dysfunctional cell or tumor, and via its Fc domain the antibody or mAb is capable of binding to or interacting with a macrophage, monocyte, microglial cell, osteoclast, Kupffer cell or dendritic cell FcγR receptor capable of initiating phagocytosis of the cancer or dysfunctional cell or tumor; and (c) exposing or contacting, or having exposed or having contacted, the cancer or dysfunctional cell or tumor to the antibody or mAb, wherein when the exposure is in vivo and the exposure comprises administering or having administered to an individual in need thereof the antibody or mAb, wherein optionally the antibody or mAb is administered in situ in or near the cancer or tumor or dysfunctional cell, or by injection (optionally intravenously (IV), intraperitoneally (IP), or intramuscularly (IM)) to the individual in need thereof, wherein optionally the antibody or mAb administration in situ in or near the cancer or tumor or dysfunctional cell is by injection or by implanting a device (an implant) comprising the antibody or mAb, and optionally the dosage of the antibody or mAb is between about 0.1 to 1000 µg/ml, and optionally when the exposure is in vivo or to an individual in need thereof the method comprises:
(i) preparing or having prepared a Shp2-iSNAP chimeric protein-expressing engineered macrophage, monocyte, microglial cell, osteoclast, Kupffer cell or dendritic cell ex vivo and administering or having administered a Shp2-iSNAP chimeric protein-expressing engineered macrophage, monocyte, microglial cell, osteoclast, Kupffer cell or dendritic cell in vivo or to the individual in need thereof, wherein optionally between about $10^3$ to $10^4$ to about $5 \times 10^6$ to $5 \times 10^8$ engineered macrophage, monocyte, microglial cell, osteoclast, Kupffer cell or dendritic cells are administered per unit dosage, optionally administered intravenously (IV), intraperitoneally (IP), intrathecally, or intramuscularly (IM), optionally the administration is by in situ injection or deposition (optionally by or via an implant), wherein optionally the Shp2-iSNAP chimeric protein-expressing engineered macrophage, monocyte, microglial cell, osteoclast, Kupffer cell or dendritic cell is administered in situ in or near the cancer or tumor or dysfunctional cell, wherein optionally the Shp2-iSNAP chimeric protein-expressing engineered macrophage, monocyte, microglial cell, osteoclast, Kupffer cell or dendritic cell administration in situ in or near the cancer or tumor or dysfunctional cell is by injection or by implanting a device (an implant) comprising the Shp2-iSNAP chimeric protein-expressing engineered macrophage, monocyte, microglial cell, osteoclast, Kupffer cell or dendritic cell, or (ii) engineering or having engineered a macrophage, monocyte, microglial cell, osteoclast, Kupffer cell or dendritic cell in vivo by administering or having administered to the individual in need thereof a nucleic acid encoding the Shp2-iSNAP chimeric protein, wherein optionally the nucleic acid is contained in a gene therapy vector or virus (or the expression vehicle or cassette, a vector, a virus, or a plasmid as provided herein, which optionally is designed to target a macrophage, monocyte, microglial cell, osteoclast, Kupffer cell or dendritic cell), wherein the nucleic acid is expressed in the macrophage, monocyte, microglial cell, osteoclast, Kupffer cell or dendritic cell thereby causing it to express the Shp2-iSNAP chimeric protein.

In alternative embodiments, provided are methods for:

cancer cell or tumor eradication in an individual in need thereof, for treating or ameliorating a cancer or a tumor or a condition caused by a dysfunctional cell, promoting development of an M1 macrophage phenotype, or for promoting an anti-cancer, anti-tumor or anti-dysfunctional cell inflammatory response, in an individual in need thereof, the method comprising:

(a) administering or having administered to the individual in need thereof an antibody or mAb capable of specifically binding to the cancer cell, tumor or dysfunctional cell, the administration as set forth in any method or embodiment as provided herein, e.g., intravenously (IV), intrathecally, intraperitoneally (IP), or intramuscularly (IM), and (b) (i) preparing or having prepared a Shp2-iSNAP chimeric protein-expressing engineered macrophage, monocyte, microglial cell, osteoclast, Kupffer cell or dendritic cell as provided herein ex vivo and administering or having administered the Shp2-iSNAP chimeric protein-expressing engineered macrophage, monocyte, microglial cell, osteoclast, Kupffer cell or dendritic cell in vivo or to the individual in need thereof, or (ii) engineering or having engineered a macrophage, monocyte, microglial cell, osteoclast, Kupffer cell or dendritic cell in vivo by administering or having administered to the individual in need thereof a nucleic acid encoding the Shp2-iSNAP chimeric protein, wherein optionally the nucleic acid is contained in a gene therapy vector or virus (or the expression vehicle or cassette, a vector, a virus, or a plasmid of claim 4, which optionally is designed to target a macrophage, monocyte, microglial cell, osteoclast, Kupffer cell or dendritic cell), wherein the nucleic acid is expressed in the macrophage, monocyte, microglial cell, osteoclast, Kupffer cell or dendritic cell thereby causing it to express (to express extracellularly an extracellular domain of) the Shp2-iSNAP chimeric protein.

In alternative embodiments, provided are Uses of a Shp2-iSNAP chimeric protein-expressing engineered macrophage, monocyte, microglial cell, osteoclast, Kupffer cell or dendritic cell for:

a cancer cell or a tumor eradication, promoting the development of an M1 macrophage phenotype, for the treatment or amelioration of a cancer, a tumor or a condition or disease caused by a dysfunctional cell, or for promoting an anti-cancer, anti-tumor or anti-dysfunctional cell inflammatory response, in an individual in need thereof, wherein the Shp2-iSNAP chimeric protein-expressing engineered macrophage, monocyte, microglial cell, osteoclast, Kupffer cell or dendritic cell is an engineered cell of any of the preceding claims, and the cancer, tumor or dysfunctional cell is eradicated, treated or ameliorated in the individual in need thereof by practicing a method of any of the preceding claims.

In alternative embodiments, provided are Shp2-iSNAP chimeric protein-expressing engineered macrophages, monocytes, microglial cells, osteoclasts, Kupffer cells or dendritic cells for use in:

a cancer cell or a tumor eradication, for the treatment or amelioration of a cancer, a tumor or a condition or disease caused by a dysfunctional cell, or for promoting an anti-cancer, anti-tumor or anti-dysfunctional cell inflammatory response, in an individual in need thereof, wherein the Shp2-iSNAP chimeric protein-expressing engineered macrophage or dendritic cell is an engineered cell of any of the preceding claims, and the cancer cell or tumor is eradicated in the individual in need thereof by practicing a method of any of the preceding claims.

In alternative embodiments, provided are kits comprising an engineered eukaryotic cell as provided herein (e.g., a macrophage, monocyte, microglial cell, osteoclast, Kupffer cell or dendritic cell), where the kit optionally comprising instructions for practicing a method of any of the preceding claims, or the kit optionally further comprises an antibody or mAb capable of specifically binding to the cancer cell, tumor or dysfunctional cell, or the kit optionally further comprises any component for practicing a method of any of the preceding claims.

In alternative embodiments, provided are products (or articles) of manufacture comprising an engineered eukaryotic cell as provided herein, wherein optionally the product of manufacture is: a device; an implant; a vial, a carpule or storage container; or a catheter.

In alternative embodiments, in practicing methods as provided herein the cancer or tumor can be: a lung cancer, melanoma, breast cancer, prostate cancer, colon cancer, renal cell carcinoma, ovarian cancer, neuroblastoma, rhabdomyosarcoma, leukemia or lymphoma, Hodgkin's lymphoma or childhood acute lymphoblastic leukemia, a mastocytoma or a mast cell tumor, an ovarian cancer or carcinoma, pancreatic cancer, a non-small cell lung cancer, small cell lung cancer, hepatocarcinoma, melanoma, retinoblastoma, breast tumor, colorectal carcinoma, leukemia, lymphoma, acute lymphoblastic leukemia (ALL) or acute lymphoid leukemia, acute myeloid leukemia (AML), a histiocytic sarcoma, a brain tumor, an astrocytoma, a glioblastoma, a neuroma, a colon carcinoma, cervical carcinoma, sarcoma, bladder tumor, tumor of the reticuloendothelial tissues, Wilm's tumor, a bone cancer, an osteosarcoma, a renal cancer, or head and neck cancer, oral cancer, a laryngeal cancer, or an oropharyngeal cancer.

In alternative embodiments, in practicing methods as provided herein the antibody or the mAb is selected from the group consisting of (or, can be) an anti-IGF-1R (e.g., hR1) ( ), an anti-mucin (e.g., hPAM4 or KC4), an anti-CD20 (e.g., rituximab, tositumomab, ibritumomab tiuxetan, GA101 or hA20), an anti-CD19 (e.g., hA19), an anti-AFP (e.g., hIMMU31), an anti-CD74 (e.g., hLL1), an anti-CD22 (e.g., hLL2 or RFB4), an anti-CSAp (e.g., hMu-9), an anti-HLA-DR (e.g., hL243), an anti-CEACAM-5 (e.g., hMN-14), an anti-CEACAM-6 (e.g., hMN-15 or hMN-3 ( ), an anti-TROP-2 (e.g., hRS7), an anti-TAG-72 (e.g., CC49), an anti-PSMA (e.g., J591 or D2/B), an anti-carbonic anhydrase IX (e.g., G250), an anti-TNF-α (e.g., infliximab or certolizumab pegol, or adalimumab), anti-CD52 (e.g., alemtuzumab), anti-VEGF (e.g., bevacizumab), anti-EGFR (e.g., panitumumab or cetuximab), anti-CD33 (e.g., gemtuzumab), anti-HER2/neu (e.g., trastuzumab), anti-IL-6 receptor (e.g., tocilizumab, anti-CD25 (e.g., basiliximab or daclizumab), anti-CD11a (e.g., efalizumab), anti-CD3 receptor (e.g., muromonab-CD3), anti-a4 integrin (e.g., natalizumab), anti-histone H2A/H4 (e.g., BWA-3), anti-histone H3 (e.g., LG2-1), an anti-histone H1 (e.g., MRA12), an anti-histone H2B (e.g., PR1-1, LG11-2, LG2-2).

In alternative embodiments, in practicing methods as provided herein the antibody or the mAb specifically targets an antigen selected from the group consisting of α-fetoprotein (AFP), α-actinin-4, A3, antigen specific for A33 antibody, ART-4, B7, Ba 733, BAGE, BrE3-antigen, CA125, CAMEL, CAP-1, carbonic anhydrase IX, CASP-8/m, CCL19, CCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD66a-e, CD67, CD70, CD70L, CD74, CD79a, CD79b, CD80, CD83, CD95, CD126, CD132, CD133, CD138, CD147, CD154, CDC27, CDK-4/m, CDKN2A, CTLA4, CXCR4, CXCR7, CXCL12, HIF-1α, colon-specific antigen-p (CSAp), CEA (CEACAM-5), CEACAM-6, c-Met, DAM, EGFR, EGFRvIII, EGP-1 (TROP-2), EGP-2, ELF2-M, Ep-CAM, fibroblast growth factor (FGF), Flt-1, Flt-3, folate receptor, G250 antigen, GAGE, gp100, GRO-β, HLA-DR, HM1.24, human chorionic gonadotropin (HCG) and its subunits, HER2/neu, HMGB-1, hypoxia inducible factor (HIF-1), HSP70-2M, HST-2, Ia, IGF-1R, IFN-γ, IFN-α, IFN-β, IFN-λ, IL-4R, IL-6R, IL-13R, IL-15R, IL-17R, IL-18R, IL-2, IL-6, IL-8, IL-12, IL-15, IL-17, IL-18, IL-23, IL-25, insulin-like growth factor-1 (IGF-1), KC4-antigen, KS-1-antigen, KS1-4, Le-Y, LDR/FUT, macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUC5ac, MUC13, MUC16, MUM-1/2, MUM-3, NCA66, NCA95, NCA90, pancreatic cancer mucin, PD1 receptor, placental growth factor, p53, PLAGL2, prostatic acid phosphatase, PSA, PRAME, PSMA, P1GF, ILGF, ILGF-R, L-6, IL-25, RS5, RANTES, T101, SAGE, S100, survivin, survivin-2B, TAC, TAG-72, tenascin, TRAIL receptors, TNF-α, Tn antigen, Thomson-Friedenreich antigens, tumor necrosis antigens, VEGFR, ED-B fibronectin, WT-1, 17-1A-antigen, complement factors C3, C3a, C3b, C5a, C5, an angiogenesis marker, bcl-2, bcl-6, and Kras.

The details of one or more exemplary embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

DESCRIPTION OF DRAWINGS

The drawings set forth herein are illustrative of exemplary embodiments provided herein and are not meant to limit the scope of the invention as encompassed by the claims.

FIG. 1A illustrates a schematic drawing of the Shp2-iSNAP and its putative activation mechanism;

FIG. 1B illustrates a schematic drawing of the SIRPα Shp2-iSNAP and its putative activation mechanism upon engagement of CD47;

FIG. 1C illustrates a schematic of SIRPα Syk-iSNAP, where the activated kinase domain is labeled "Kin" (and colored in red);

FIG. 1D illustrates a schematic of engineering macrophages for mAbs-guided cancer cell eradication;
as described in detail, below.

FIG. 2A graphically illustrates the emission spectrum change of the Shp2-iSNAP before (black) and after (red) Src kinase incubation in vitro;

FIG. 2B-C graphically illustrate the emission ratio time courses (FIG. 2B) and phosphatase activities (FIG. 2C) of Shp2-iSNAP and its FF mutant before and after Src incubation in vitro as indicated;

FIG. 2D illustrates ratiometric images of a MEF cell transfected with the Shp2-iSNAP before and after PDGF stimulation at indicated time points;

FIG. 2E graphically illustrates the ratio time courses (mean±S.E.M) of MEFs expressing the Shp2-iSNAP or its FF mutants;

FIG. 2F illustrates a schematic drawing of the inhibitory effect of the non-fluorescent Shp2-iSNAP upon activation on its target FAK monitored by a membrane-bound FAK biosensor;

FIG. 2G illustrates bar graphs of FAK biosensor emission ratios (mean±S.E.M) in PDGF-stimulated MEFs expressing control vector, the Shp2-iSNAP, or its FF mutant; *, P<0.05 (n=3), as described in detail, below.

FIG. 3A schematically illustrates the SIRPα Shp2-iSNAP and its putative activation mechanism upon engagement of CD47;

FIG. 3B illustrates ratiometric, YPet, and Differential Interference Contrast (DIC) images of RAW264.7 macrophages expressing SIRPα Shp2-iSNAP or FF mutant after incubation with beads coated by CD47 plus IgG, CD47 only, or IgG only, respectively;

FIG. 3C graphically illustrates quantification of local FRET response in macrophages stimulated by beads with different coatings as indicated in FIG. 3B;

FIG. 3D graphically illustrates the time course of FRET ratio of SIRPα Shp2-iSNAP in response to CD47-coated beads and 10 μM SFKs inhibitor PP1 treatment;

FIG. 3E illustrates Ratiometric, YPet, and DIC images of phagocytosis of opsonized RBCs by a representative RAW264.7 macrophage expressing SIRPα Shp2-iSNAP at indicated time points;

FIG. 3F graphically illustrates a Bar graph (mean±S.E.M.) of normalized phagocytic rate of macrophages expressing SIRPα Shp2-iSNAP or its controls against the opsonized RBCs at 37° C. for 30 min, FF mutations in the BTAM peptide of iSNAP; "APTP", SIRPα Shp2-iSNAP without PTP domain; "SIRP", full length SIRPα fused with YPet; "SIRP-no ITIM", ITIM-truncated SIRPα fused with YPet, as described in detail, below.

FIG. 4A and FIG. 4D illustrate Ratiometric, YPet, and DIC images of a representative BMDM expressing exemplary chimeric SIRPα Shp2-iSNAP proteins before and after incubation with 10 µg/ml rituximab-opsonized Toledo cells (FIG. 4A) or 2 µg/ml cetuximab-opsonized DLD1 (FIG. 4D) at indicated time points;

FIG. 4B graphically illustrates the time course of FRET ratio of SIRPα Shp2-iSNAP in the BMDM at the region around the engaging Toledo cell in (FIG. 4A);

FIG. 4C and FIG. 4E graphically illustrates a Bar graph (mean±S.E.M.) of normalized phagocytic rate of macrophages expressing different constructs as described in FIG. 3 against rituximab-opsonized Toledo (C) or cetuximab-opsonized DLD1 cells (E).

FIG. 5A schematically illustrates a SIRPα Syk-iSNAP and its putative activation mechanism (activation of kinase, or "Kim") upon CD47 engagement by phosphorylation of the BTAM2 motif;

FIG. 5B illustrates Ratiometric, YPet, and DIC images of RAW264.7 macrophages expressing SIRPα Syk-iSNAP before and after incubation with CD47-coated beads;

FIG. 5C illustrates Ratiometric and DIC images of RAW264.7 macrophages expressing dark SIRPα Syk-iSNAP together with $Ca^{2+}$ or Erk FRET biosensors before and after the incubation with CD47-coated beads;

FIG. 5D illustrates Ratiometric and DIC images of phagocytic processes of opsonized RBCs by a representative RAW264.7 macrophage expressing SIRPα Syk-iSNAP;

FIG. 5E graphically illustrates a Bar graph (mean±S.E.M.) of normalized phagocytic rate of RAW264.7 macrophages expressing SIRPα Syk-iSNAP or control constructs against the rabbit anti-human RBC IgG-opsonized RBCs at 37° C. for 30 min; FF, FF mutations in the BTAM peptide of iSNAP; K402R, a kinase dead mutant K402R in Syk kinase domain of iSNAP; other constructs are the same as described for FIG. 3, as described in detail, below.

FIG. 6A: illustrates a schematic drawing of an activation mechanism for phagocytosis in the iSNAP-engineered monocytes;

FIG. 6B illustrates fluorescence images of YFP signals in the iSNAP proteins stably expressed in the engineered THP1 monocytes;

FIG. 6C illustrates flow cytometry results of YFP signals in the iSNAP proteins stably expressed in the exemplary engineered THP1 monocytes to quantify the expression of iSNAPs;

FIG. 6D graphically illustrates quantification of mRNA levels of endogenous SIRPα receptors and exemplary engineered-iSNAP in THP1 cells, as described in detail, below.

FIG. 7A graphically illustrates the expression of lineage markers in the control and exemplary iSNAP-engineered THP1 monocytes. CD31: monocyte marker; CD11b and CD14: macrophage markers;

FIG. 7B graphically illustrates the expression of macrophage polarization markers in the control and exemplary iSNAP-engineered THP1 monocytes. CD68, CD80, CD86: M1 macrophage polarization markers; CD163, CD206: M2 macrophage polarization markers;

FIG. 7C graphically illustrates the expression of macrophage pro-inflammatory cytokines in the control and exemplary iSNAP-engineered THP1 monocytes, IL-6 and TNFa: pro-inflammatory cytokine markers; IL-10: anti-inflammatory cytokine marker, as described in detail, below.

FIG. 8A schematically illustrates the treatment of human B-lymphoma (Toledo) tumors in nude mice models by exemplary iSNAP-engineered macrophages as provided herein and control THP1 cells, guided by Rituximab recognizing Toledo antigen CD20;

FIG. 8B graphically illustrates the time course quantification of B-lymphoma tumor sizes after the treatment by exemplary iSNAP-engineered and control THP1 cells, guided by Rituximab recognizing Toledo antigen CD20, as described in detail, below.

Like reference symbols in the various drawings indicate like elements.

DETAILED DESCRIPTION

Figure 1:
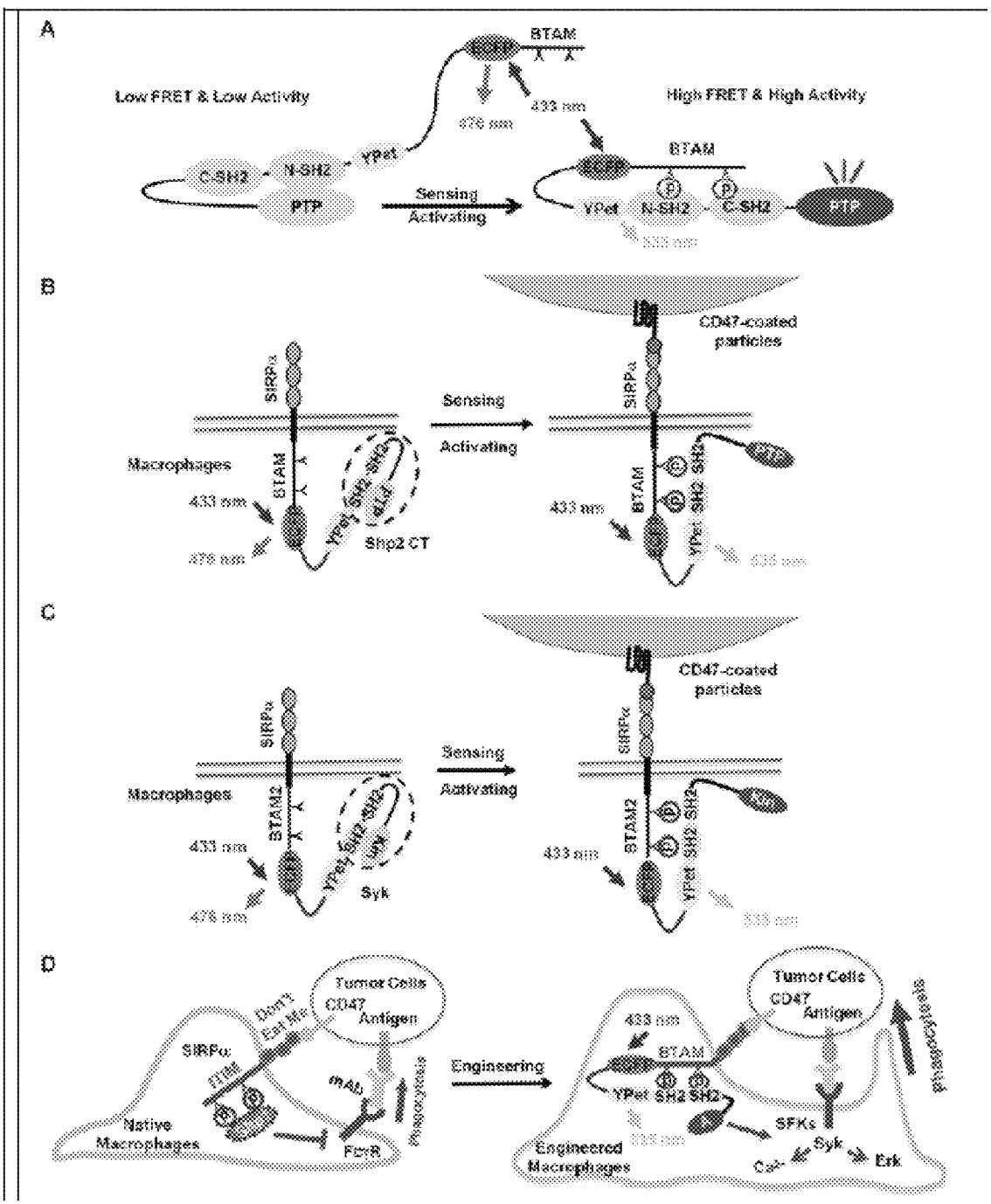
FIG. 1A-D illustrate the designation, activation mechanism and functionality of the iSNAP, SIRPα Shp2-iSNAP and SIRPα Syk-iSNAP engineered proteins and constructs as provided herein.

In alternative embodiments, provided are engineered immune cells, including macrophages, monocytes, dendritic cells, microglia, osteoclasts and Kupffer cells comprising chimeric Signal Regulatory Protein α (SIRPα) integrated sensing and actuating proteins (iSNAPs), and methods for making and using them. In alternative embodiments, provided is a Shp2- and Syk-integrated sensing and actuating protein (iSNAP) (Src homology region 2 domain-containing phosphatase-2 (Shp-2)- and Syk-iSNAP) chimeric protein comprising: a phosphorylatable peptide (e.g., a bi-phosphorylatable peptide, optionally a bisphosphoryl tyrosine-based activation (BTAM) motif; a Fluorescent Protein (FP) Förster Resonance Energy Transfer (FRET) (or FP FRET) pair or pair of motifs, and optionally an enhanced cyan fluorescent protein (ECFP) motif and a YPet fluorochrome; a truncated Shp2 domain comprising an N-SH2 domain and a C-SH2 domain; and, a phosphatase (PTP) domain or a kinase domain. Also provided are methods and uses for enhancing macrophage-, monocyte-, dendritic cell-, microglia-, osteoclast- or Kupffer cell-mediated antibody- or monoclonal antibody (mAb)-mediated inflammatory responses, including enhancing guided cancer cell, dysfunctional cell or tumor eradication.

In alternative embodiments, engineered macrophages, monocytes, dendritic cells, microglia, osteoclasts and Kupffer cells with (expressing) chimeric Signal Regulatory Protein α (SIRPα) integrated sensing and actuating proteins (iSNAPs) as provided herein are used to target different types of cancers, tumors or dysfunctional cells, and in alternative embodiments, this tumor, cancer or dysfunctional cell targeting is integrated with monoclonal antibody (mAb)-mediated immunotherapy, including e.g., cancer immunotherapy, or immunotherapy for any condition caused by a dysfunctional cell.

In alternative embodiments, the Signal Regulatory Protein α (SIRPα) integrated sensing and actuating proteins (iSNAPs) and engineered cells provided herein use are used platforms for the high throughput screening of potential SIRPα inhibitors for cancer, tumor or dysfunctional cell therapy, e.g., to enhance the efficiency of therapeutic mAbs (e.g. anti-CD19, anti-CD20, anti-PSMA mAbs) against any cell target, including tumor or cancer cells, or any dysfunctional cell, including infected cells, e.g., viral or bacterium infected cells.

In alternative embodiments, chimeric SIRPα iSNAPs as provided herein are used as biosensors to study the activation and regulation of SIRPα and related molecular mechanism.

In alternative embodiments, provided herein are fluorescent protein-based biosensors and controllable protein actuators that are engineered to visualize and manipulate, respectively, signaling events in live cells as separate, parallel approaches. Here we integrate protein modules with sensing and actuating functions to engineer integrated sensing and actuating proteins (iSNAPs) capable of detecting tyrosine phosphorylation events and activating desired enzymatic domains to reprogram the cell. An iSNAP utilizing Shp2 phosphatase as the actuator (Shp2-iSNAP) was characterized and connected to the macrophage SIRPα receptor, whose native form transduces a "don't eat me" signal from CD47 ligand during phagocytosis. The macrophages engineered with this SIRPα Shp2-iSNAP not only allowed visualization of spatiotemporal dynamics of SIRPα phosphorylation upon CD47 engagement, but also rewired the detected input into the activation of positive Shp2 signaling, leading to enhanced phagocytosis of opsonized tumor cells.

Since the design of iSNAPs is highly modular, we further replaced the sensor and actuator domains in Shp2-iSNAP to create a Syk-iSNAP, which likewise rewired the CD47/SIRPα axis to the pro-phagocytic Syk kinase activation when fused to SIRPα. Thus, our approach can be extended to execute a broad range of sensing and automated reprogramming actions for macrophage engineering and directed cell, e.g., tumor, cancer or dysfunctional cell, immunotherapeutics.

In alternative embodiments, the dysfunctional cell is an infected cell, e.g., a viral or bacterium infected cell, or a cell made dysfunctional by a genetic or inherited condition.

The novel engineered integrated sensing and actuating proteins (iSNAPs) provided herein, and the engineering of macrophages by iSNAPs as provided herein, provide new immunotherapies. Previously, numerous genetically encoded biosensors based on fluorescent proteins (FPs) and FRET have been generated to visualize dynamics of signal transduction in live cells at subcellular levels (Wang, Shyy et al. 2008). In parallel, synthetic proteins that can undergo dimerization or allosteric conformational change upon stimulation by radio wave, light, chemical compounds, or cell-cell interactions have been designed to actuate signal cascades and control cellular behavior for therapeutic purposes (Toettcher, Voigt et al. 2011; Toettcher, Weiner et al. 2013; Chakravarti and Wong 2015; Wu, Roybal et al. 2015; Wu, Rupp et al. 2015; Roybal, Rupp et al. 2016). However, these two separate approaches have not been integrated into one platform to engineer proteins with both sensing and actuating functions. The new designs as provided herein combine the advantage of those approaches using integrated sensing and actuating proteins (iSNAPs) to survey the intracellular space, and to trigger designed molecular actions upon detection and visualization of specific signals, with the consequences of modulating the downstream signaling cascades and cellular (e.g., macrophage, monocyte, microglia, osteoclast, Kupffer cell or dendritic cell) functions.

In alternative embodiments, compositions and methods provided herein solve the problem of anti-CD47-based therapies, where CD47, being expressed at high levels in red blood cells (RBCs), may cause undesirable anemia may complicate anti-CD47 cancer therapy. By using engineering macrophages, monocytes, microglia, osteoclasts and Kupffer cells or dendritic cells by iSNAP with rewired CD47 signaling, as provided herein, together with monoclonal antibodies (mAbs) to specifically target a tumor, a cancer or any dysfunctional cell, provided herein is a revolutionary next-generation immunotherapy.

In alternative embodiments, provided herein is an engineered class of iSNAPs that can sense specific biochemical events and consequently activate the reprogramming of cellular (e.g., macrophage, monocyte, microglia, osteoclast, Kupffer cell or dendritic cell) functions. We first engineered a Shp2-based iSNAP (Shp2-iSNAP) for the sensing of intracellular tyrosine phosphorylation and the consequent activation of an important phosphatase (PTP) Shp2 (Tonks 2006). Structurally, the enzymatic PTP domain of Shp2 is masked by the auto-inhibitory N-SH2, which can be released upon binding of a phosphorylated peptide (Tonks 2006). We have hence fused a phosphorylatable peptide (bisphosphoryl tyrosine-based activation motif, BTAM) with a FRET pair (ECFP and YPet) and truncated Shp2 to eliminate the potential interfering binding of the truncated C-terminal tyrosine-containing tail toward the N-SH2 within the iSNAP (FIG. 1A). As such, the peptide upon kinase phosphorylation can bind to the N-SH2 domain to cause FRET changes and subsequently relieve the inhibitory effect of N-SH2 on the PTP domain, thus activating Shp2. Hence, FRET signals of the sensor module within iSNAPs can provide immediate readings and serve as "digital multimeters" for functional calibration and optimization of engineered iSNAPs. When Shp2-iSNAP was fused to the C-tail truncated SIRPα (SIRPα and Shp2-iSNAP), it could sense CD47 induced phosphorylation of SIRPα and initialize positive Shp2 action (FIG. 1B).

In one embodiment, this modular approach is used to engineer a new type of iSNAPs employing spleen tyrosine kinase (Syk) (Syk-iSNAP) (FIG. 1C).

We further applied those SIRPα iSNAPs to engineer macrophages, and this engineered macrophage was activated by CD47 expressed on tumor cells and promoted the antibody-mediated tumor cell phagocytosis comparing to native macrophage (FIG. 1D).

FIG. 1 schematically illustrates a diagram describing the designation, activation mechanism and functionality of exemplary Shp2-iSNAP, SIRPα Shp2-iSNAP, SIRPα Syk-iSNAP chimeric proteins as provided herein; this drawing schematically illustrates the designation, activation mechanism and functionality of the iSNAP, SIRPα Shp2-iSNAP and SIRPα Syk-iSNAP engineered proteins and constructs as provided herein:

(A) Schematic drawing of the Shp2-iSNAP and its putative activation mechanism. Shp2-iSNAP consists of a phosphorylatable peptide, a FP FRET pair, a truncated Shp2 consisting of two SH2 domains (N-SH2 and C-SH2) and a PTP domain. Two sensing tyrosine sites are indicated as Y (without phosphorylation), P indicates phosphorylation, activated PTP domain is colored in red.

(B) Schematic drawing of the SIRPα Shp2-iSNAP and its putative activation mechanism upon engagement of CD47. Structurally, SIRPα Shp2-iSNAP contains a human SIRPα without its ITIM-containing C-tail, fused to the Shp2-iSNAP. At rest, PTP domain is quenched by its SH2 domains. Upon CD47 stimulation, tyrosines in BTAM motif will be phosphorylated to bind SH2 domains and result in the release and activation of the PTP domain.

(C) SIRPα Syk-iSNAP has similar design with BTAM2 instead of BTAM, Syk instead of Shp2. Activated kinase domain is colored in red.

(D) Engineering macrophage for mAbs-guided cancer cell eradication. In native macrophages, pro-phagocytic activities mediated by the antigen-recognizing antibody and FcγR is inhibited by CD47-SIRPα signal pathway via the recruitment of negative regulator Shp1. In engineered macrophages, the anti-phagocytic signals of CD47-SIRPα axis are rewired by SIRPα iSNAPs to promote phagocytic activities for the tumor cell eradication.

Characterize Cytosolic Shp2-iSNAP In Vitro and in Mammalian Cells

To characterize the exemplary cytosolic Shp2-iSNAP, purified Shp2-iSNAP was incubated with recombinant Src, a kinase known to phosphorylate SIRPα in response to various mitogens (Tsuda, Matozaki et al. 1998). As we designed, the responsiveness of this iSNAP depended upon phosphorylation of tyrosines in the BTAM peptide, since mutation of these tyrosines (called an "FF" mutation) abolished phosphorylation, FRET response and PTP activation (FIG. 2A-C). When Shp2-iSNAP was expressed in mouse embryonic fibroblasts (MEFs), PDGF caused a FRET increase (FIG. 2D), which is dependent on the phosphorylatable tyrosines in the BTAM peptide (FIG. 2E). Therefore, the exemplary Shp2-iSNAP as provided herein can sense and report PDGFR activation-induced tyrosine phosphorylation events in live cells.

We further evaluated whether the Shp2-iSNAP can rewire and activate designed downstream signaling events in mouse embryonic fibroblasts (MEFs) after detecting input signals. To quantify the activation effect of the Shp2-iSNAP, we utilized a FRET-based Lyn-focal adhesion kinase (FAK) biosensor to monitor the membrane activity of FAK (FIG. 2F). As a downstream target of Shp2, FAK can be dephosphorylated at Y397 to inhibit its kinase activity (Seong, Ouyang et al. 2011). To avoid interference between two pairs of enhanced cyan fluorescent protein (ECFP) and YPet in the same cell, we mutated the ECFP (W65A/W66A) and YPet (G66A) in the Shp2-iSNAP to eliminate its fluorescence while leaving the other domains and functions intact (FIG. 2F). Shp2-iSNAP significantly reduced PDGF-induced FAK activity compared to empty vector or the FF mutant (FIG. 2G). These results confirmed the designed functionality of Shp2-iSNAP in vitro and in live cells.

Figure 2:
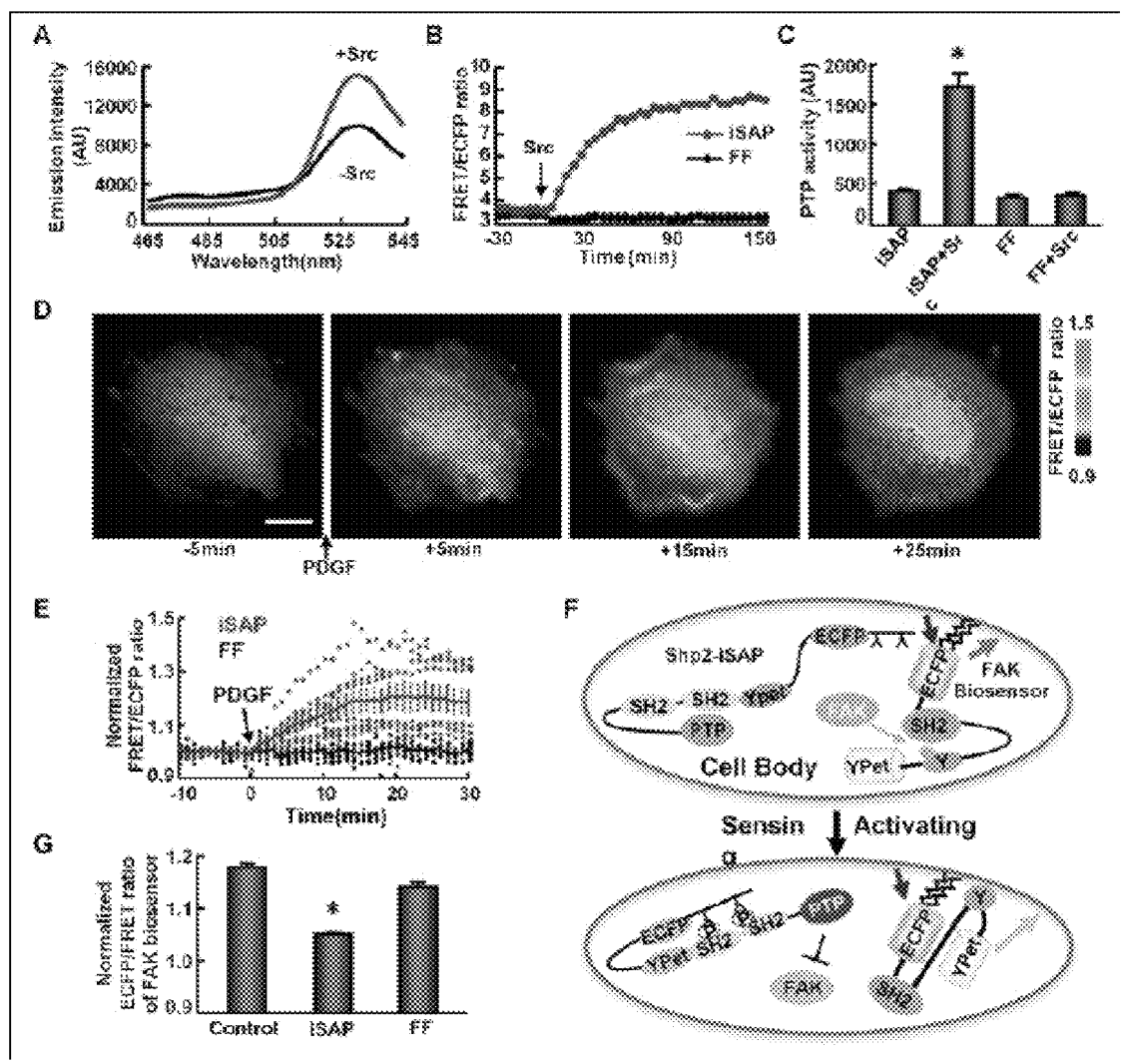
FIG. 2A-G illustrate the characterization of the Shp2-iSNAP in vitro and in cells.

FIG. 2 illustrates the characterization of the Shp2-iSNAP in vitro and in cells:

(A) graphically illustrates the emission spectrum change of the Shp2-iSNAP before (black) and after (red) Src kinase incubation in vitro;

(B, C) graphically illustrate the emission ratio time courses (B) and phosphatase activities (C) of Shp2-iSNAP and its FF mutant before and after Src incubation in vitro as indicated;

(D) illustrate ratiometric images of a MEF cell transfected with the Shp2-iSNAP before and after PDGF stimulation at indicated time points. Color scale bar represents the FRET/CFP emission ratio, with cold (the shading or blue coloring closer to the indicated 0.9 on the FRET/CFP scale) and hot (the shading or orange/red coloring closer to the indicated 1.5 on the FRET/CFP scale) colors representing low and high FRET efficiency of iSNAP, respectively; Size scale bar, 20 μm;

(E) graphically illustrates the ratio time courses (mean±S.E.M) of MEFs expressing the Shp2-iSNAP or its FF mutants;

(F) illustrates a schematic drawing of the inhibitory effect of the non-fluorescent Shp2-iSNAP upon activation on its target FAK monitored by a membrane-bound FAK biosensor; the activated iSNAP and FAK are colored in orange and red, respectively;

(G) illustrates Bar graphs of FAK biosensor emission ratios (mean±S.E.M) in PDGF-stimulated MEFs expressing control vector, the Shp2-iSNAP, or its FF mutant; *, P<0.05 (n=3).

SIRPα Shp2-iSNAP Activated by CD47 and Promote Phagocytic Functions in Macrophages While the native CD47-SIRPα pathway in myeloid cells is mediated by the negative regulator Shp1 (Tsai and Discher 2008), Shp2 can act as a positive regulator in macrophages (Neel, Gu et al. 2003; Matozaki, Murata et al. 2009). The fusion of Shp2-iSNAP to the C-tail of SIRPα (SIRPα Shp2-iSNAP) may rewire the anti-phagocytic "don't eat me" CD47/SIRPα/Shp1 negative signaling into a positive Shp2 action upon the engagement of CD47, thus facilitating phagocytosis of opsonized tumor cells initiated by IgG-FcγR interactions (FIG. 3A). When CD47-coated beads engaged the RAW264.7 macrophages expressing SIRPα Shp2-iSNAP, a local FRET increase of the iSNAP was observed (FIG. 3B). This activation was specific to CD47 and depended on tyrosine phosphorylation, since it was abolished in groups using beads coated with IgG only or with iSNAP FF mutant (FIG. 3B-C). Consistent with the potent capability of Src family kinases (SFKs) in phosphorylating SIRPα (Tsuda, Matozaki et al. 1998; Johansen and Brown 2007), the SFKs inhibitor PP1 markedly suppressed the FRET response of SIRPα Shp2-iSNAP (FIG. 3D).

We next examined macrophages engineered with SIRPα Shp2-iSNAP for their phagocytic activity against the human RBCs that endogenously express high levels of CD47 (Oldenborg, Zheleznyak et al. 2000). Indeed, comparing to control groups, RAW264.7 macrophages expressing SIRPα Shp2-iSNAP exhibited a significantly increased capability in engulfing opsonized-RBCs, accompanied by a transient FRET response of SIRPα Shp2-iSNAP, which returned to the basal level once the RBCs were completely engulfed by the macrophages (FIG. 3E-F). These results indicate that the rewiring of CD47 signaling by SIRPα Shp2-iSNAP can promote the phagocytic ability of the engineered macrophages toward RBCs.

Figure 3:
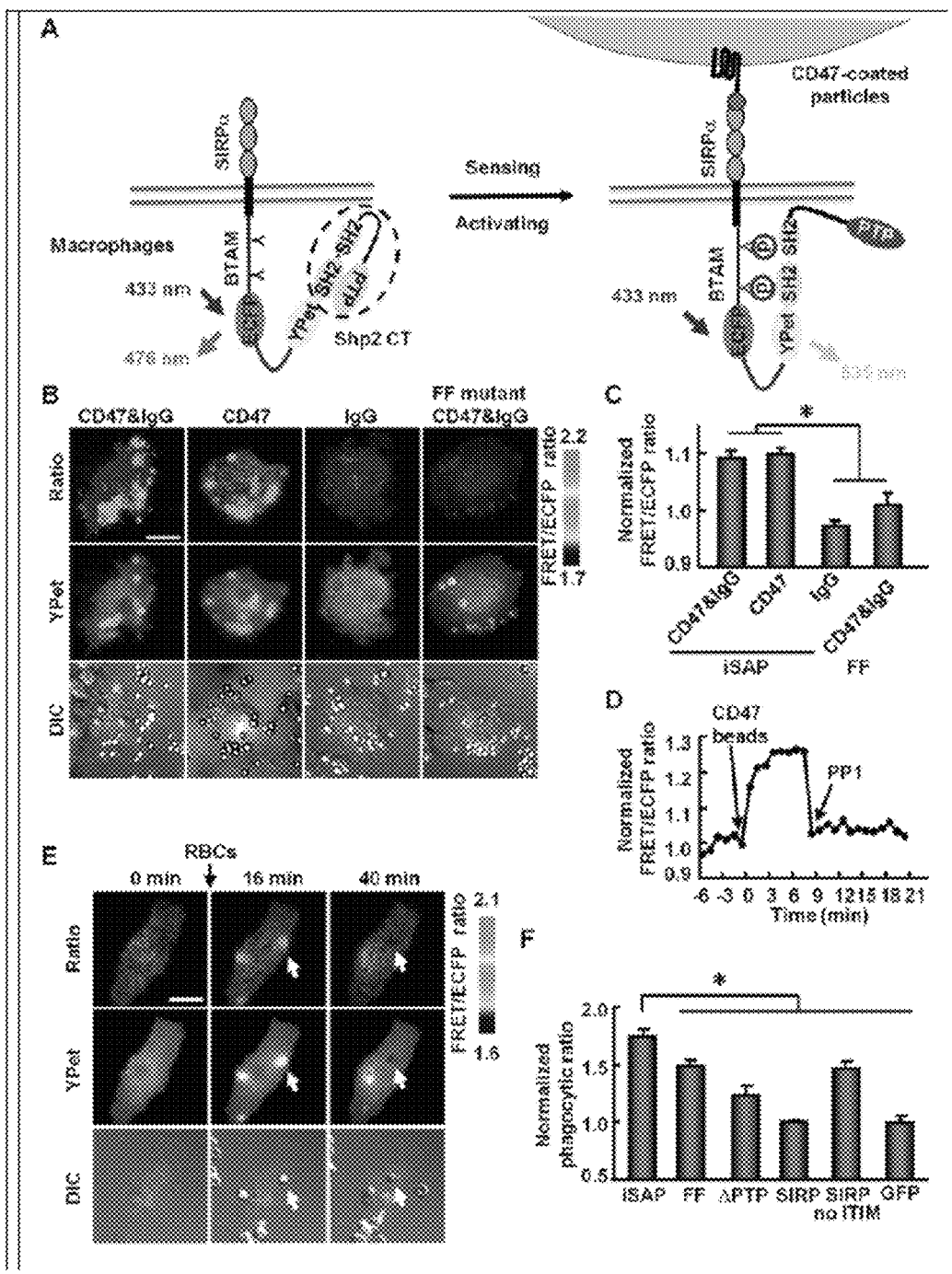
FIG. 3A-F illustrate the activation and phagocytic functions of SIRPα Shp2-iSNAP in macrophages.

FIG. 3 illustrates the activation and phagocytic functions of SIRPα Shp2-iSNAP in macrophages:

(A) schematically illustrates the SIRPα Shp2-iSNAP and its putative activation mechanism upon engagement of CD47;

(B) illustrates ratiometric, YPet, and DIC images of RAW264.7 macrophages expressing SIRPα Shp2-iSNAP or FF mutant after incubation with beads coated by CD47 plus IgG, CD47 only, or IgG only, respectively;

(C) graphically illustrates quantification of local FRET response in macrophages stimulated by beads with different coatings as indicated in (B);

(D) graphically illustrates the time course of FRET ratio of SIRPα Shp2-iSNAP in response to CD47-coated beads and 10 μM SFKs inhibitor PP1 treatment;

(E) illustrates Ratiometric, YPet, and DIC images of phagocytosis of opsonized RBCs by a representative RAW264.7 macrophage expressing SIRPα Shp2-iSNAP at indicated time points; RBCs were opsonized with anti-human RBC IgG; Arrows point to the positions of ingested RBCs;

(F) graphically illustrates a Bar graph (mean±S.E.M.) of normalized phagocytic rate of macrophages expressing SIRPα Shp2-iSNAP or its controls against the opsonized RBCs at 37° C. for 30 min, FF mutations (tyrosine mutations) in the BTAM peptide of iSNAP; "APTP", SIRPα Shp2-iSNAP without PTP domain; "SIRP", full length SIRPα fused with YPet; "SIRP-no ITIM", ITIM-truncated SIRPα fused with YPet. *: $P<0.05$; Color and size scale bars are the same as FIG. 2.

SIRPα Shp2-iSNAP Activated by CD47 and Promote Phagocytic Functions in Macrophages.

We then examined whether an exemplary chimeric SIRPα Shp2-iSNAP protein can rewire the "don't eat me" signal of CD47/SIRPα to produce engineered macrophages with high phagocytic capabilities against tumor cells expressing CD47. We then targeted two types of cancer cells expressing high levels of CD47 and tumor-specific antigens (TSAs), viz., Toledo, a human non-Hodgkin's lymphoma (NHL) cell line representing hematologic cancer that expresses CD20, and DLD1, a human colon cancer cell line representing nonhematopoietic solid tumor that expresses EGFR. The engineered bone marrow-derived macrophages (BMDMs) led to a rapid engulfment of engaged Toledo cells opsonized by anti-CD20 antibody, accompanied by a locally activated and transient FRET signals of SIRPα Shp2-iSNAP which returned to the basal level after the completion of Toledo phagocytosis (FIG. 4A-B). The mutation of sensing tyrosines or PTP domain in SIRPα Shp2-iSNAP caused a significant reduction of the phagocytic activity of the engineered BMDMs (FIG. 4C). Similar results can be observed in engineered BMDMs when they engaged with DLD1 (ATCC® CCL-221™) cells opsonized by anti-EGFR antibody (FIG. 4D-E). These results indicate that the rewiring of CD47 signaling in macrophages by an exemplary chimeric SIRPα Shp2-iSNAP can promote the antibody-mediated tumor cell phagocytosis.

Figure 4:
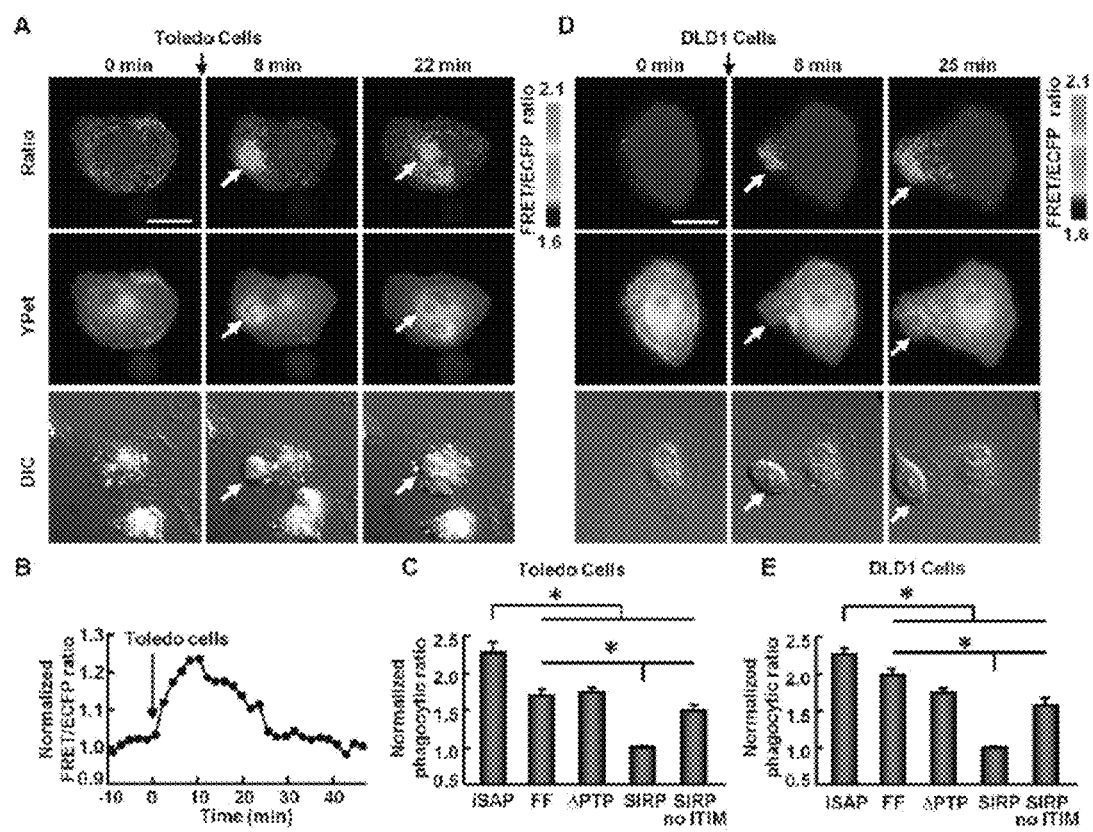
FIG. 4A-E illustrate the activation and function of exemplary chimeric SIRPα Shp2-iSNAP proteins on phagocytosis of cancer cells.

FIG. 4 illustrates the activation and function of SIRPα Shp2-iSNAP on phagocytosis of cancer cells:

Figures (A) and (D) illustrate Ratiometric, YPet, and DIC images of a representative BMDM expressing exemplary chimeric SIRPα Shp2-iSNAP proteins before and after incubation with 10 μg/ml rituximab-opsonized Toledo cells (A) or 2 μg/ml cetuximab-opsonized DLD1 (D) at indicated time points; the arrows point to the positions where opsonized tumor cells engage the engineered macrophages; the colors of the images represent the ratiometric signals of biosensors within iSNAPs, with cold and hot colors represent the low and high levels of iSNAP activations.

(B) graphically illustrates the time course of FRET ratio of SIRPα Shp2-iSNAP in the BMDM at the region around the engaging Toledo cell in (A);

(C) and (E) graphically illustrates a Bar graph (mean±S.E.M.) of normalized phagocytic rate of macrophages expressing different constructs as described in FIG. 3 against rituximab-opsonized Toledo (C) or cetuximab-opsonized DLD1 cells (E).

SIRPα Syk-iSNAP Activated by CD47 and Promote Phagocytic Functions in Macrophages.

We further extended our modular approach to engineer an exemplary chimeric protein, which is new type of iSNAP employing spleen tyrosine kinase (Syk) (Syk-iSNAP) (Mocsai, Ruland et al. 2010), with the sensing peptide derived from the ITAM (immunoreceptor tyrosine-based activation) motif of FcγRIIA followed by the same FRET pair and the full-length human Syk. Syk-iSNAP was also fused to SIRPα to develop SIRPα Syk-iSNAP (FIG. 5A). CD47-coated beads induced the FRET response of the SIRPα Syk-iSNAP (FIG. 5B). Intracellular $Ca^{2+}$ and Erk activation was detected by the $Ca^{2+0}$ and Erk FRET biosensors in RAW264.7 macrophages engineered with the dark SIRPα Syk-iSNAP (FIG. 5C). SIRPα Syk-iSNAP in engineered RAW264.7 macrophages could also be activated by opsonized RBCs to cause enhanced phagocytic activity, mediated by the tyrosine phosphorylation and the kinase domain of the iSNAP (FIG. 5C-E). Therefore, our modular design and strategies can be readily extended to engineer kinase-based iSNAPs capable of sensing, rewiring, and reprogramming cells.

Figure 5:
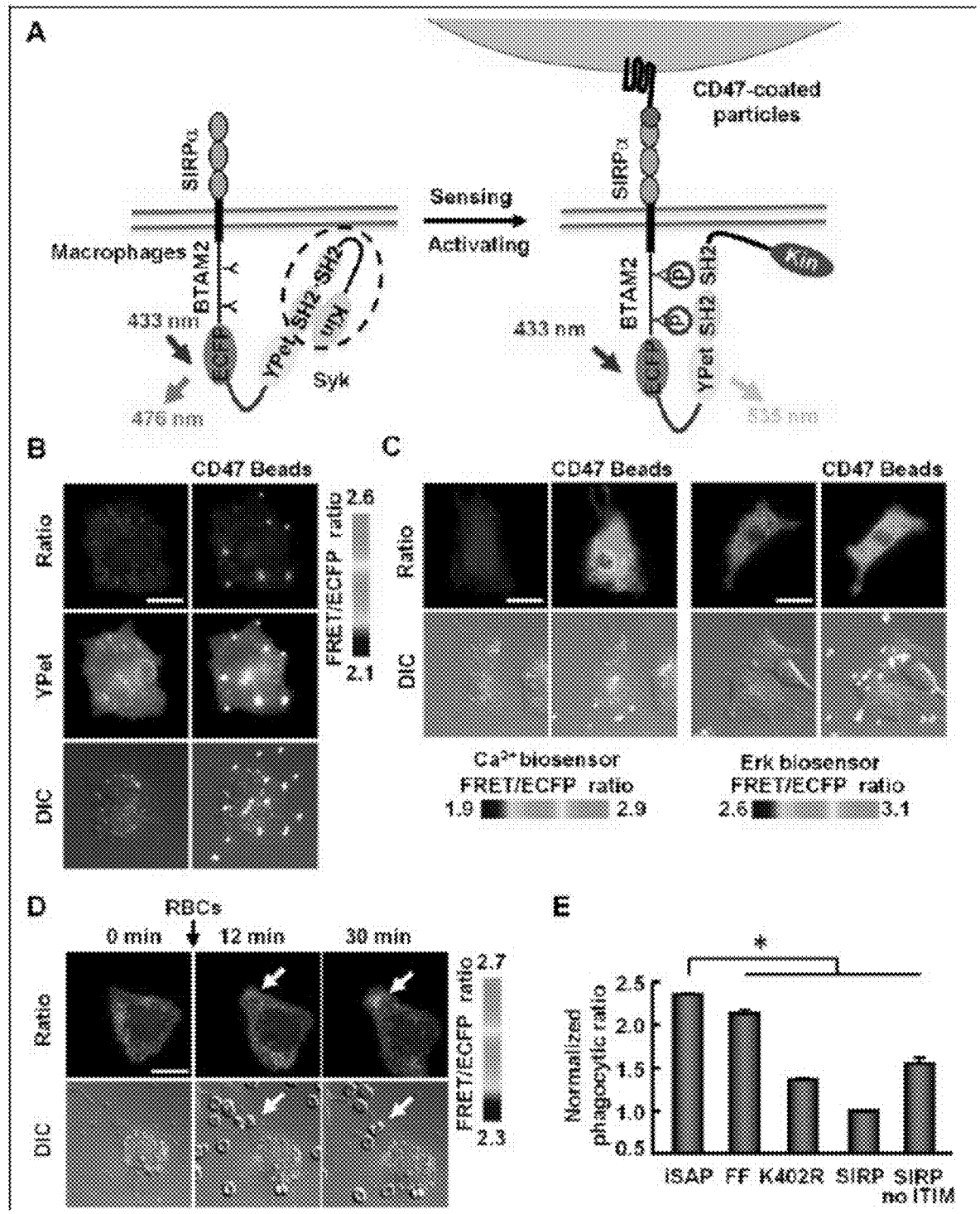
FIG. 5A-E illustrate the activation and function of exemplary chimeric SIRPα Syk-iSNAP proteins in macrophages.

FIG. 5 illustrates the activation and function of SIRPα Syk-iSNAP in macrophages:

(A) schematically illustrates a SIRPα Syk-iSNAP and its putative activation mechanism upon CD47 engagement;

(B) illustrates Ratiometric, YPet, and DIC images of RAW264.7 macrophages expressing SIRPα Syk-iSNAP before and after incubation with CD47-coated beads;

(C) illustrates Ratiometric and DIC images of RAW264.7 macrophages expressing dark SIRPα Syk-iSNAP together with $Ca^{2+}$ or Erk FRET biosensors before and after the incubation with CD47-coated beads;

(D) illustrates Ratiometric and DIC images of phagocytic processes of opsonized RBCs by a representative RAW264.7 macrophage expressing SIRPα Syk-iSNAP;

(E) illustrates a Bar graph (mean±S.E.M.) of normalized phagocytic rate of RAW264.7 macrophages expressing SIRPα Syk-iSNAP or control constructs against the rabbit anti-human RBC IgG-opsonized RBCs at 37° C. for 30 min (FF, FF mutations in the BTAM peptide of iSNAP; K402R, a kinase dead mutant K402R in Syk kinase domain of iSNAP; other constructs are the same as described in FIG. 3).

Figure 6:
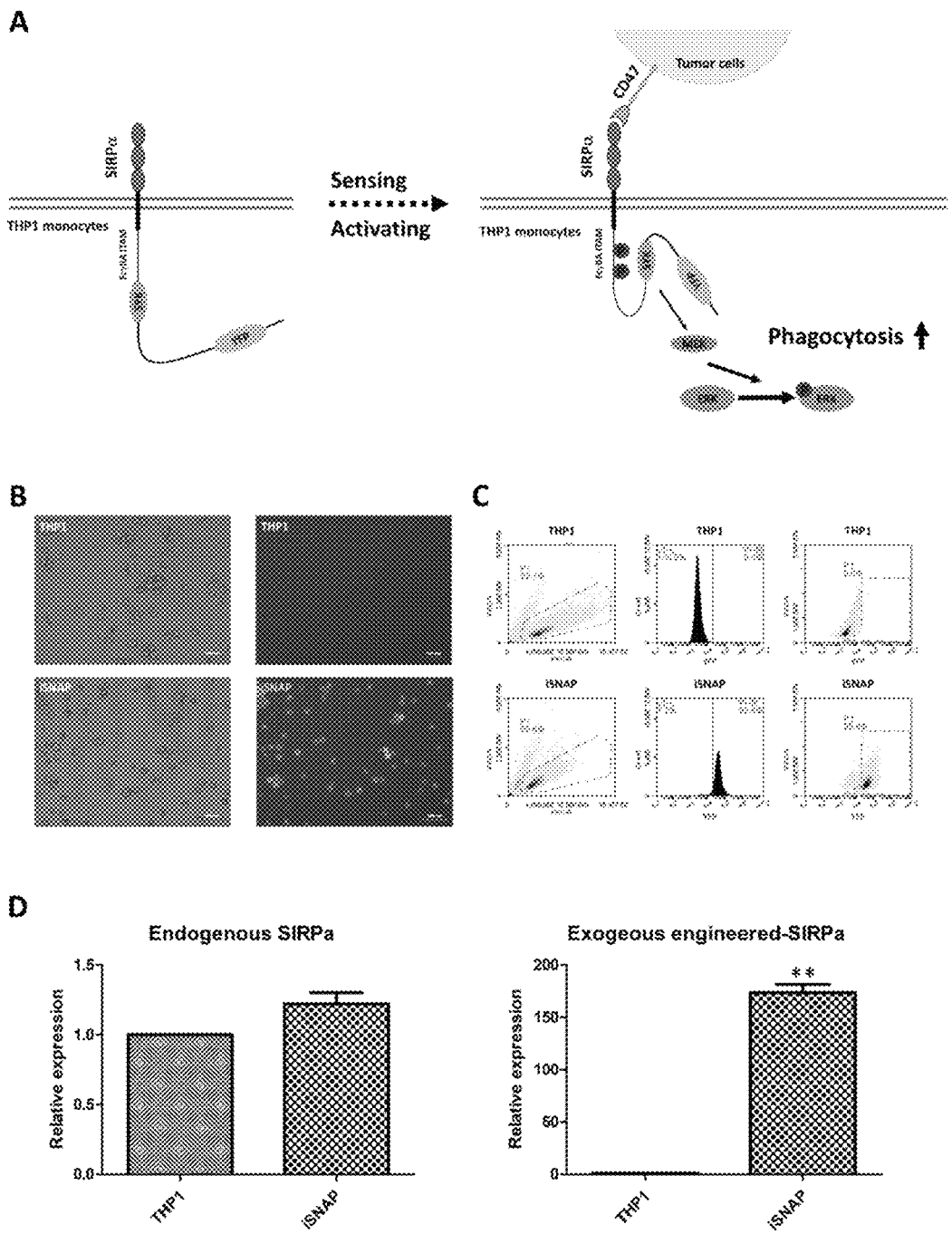
FIG. 6A-D illustrate stable expression of exemplary chimeric iSNAP proteins in engineered THP1 monocyte cell lines.

We further engineered THP1 monocyte cell lines with an exemplary iSNAP protein and examined their capability in eradicating tumors in vivo with nude mice models. As shown in FIG. 6A, the intracellular domain of SIRPα receptor was replaced by Fcγ-IA ITAM (Immunoreceptor tyrosine-based activation motif) and fused with SYK kinase, and a Ypet (YFP) reporter to generate the iSNAP construct. In the iSNAP-engineered THP1 cells, the exemplary engineered iSNAP proteins are expected to rewire the endogenous SIRPα signaling pathway and activate phagocytosis when the "don't eat me" SIRPα receptor is engaged. We have introduced the exemplary engineered iSNAP construct by lentivirus infection into THP1 monocyte cell lines. The results clearly indicate that the exemplary engineered iSNAP proteins can be stably expressed in THP1 cells, measured by both fluorescence imaging and flow cytometry (FIG. 6B-C). Quantitative PCR to measure mRNA levels of iSNAP in FIG. 6D also verified the protein expression results.

Figure 7:
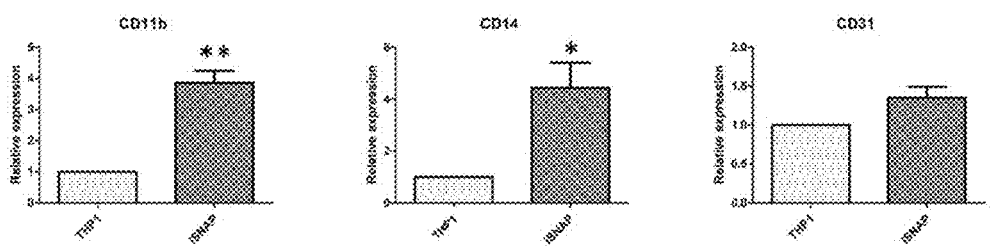
FIG. 7A-C illustrate the expression of iSNAP as provided herein affected the phenotypes of engineered THP1 monocytes.
Figure 7:
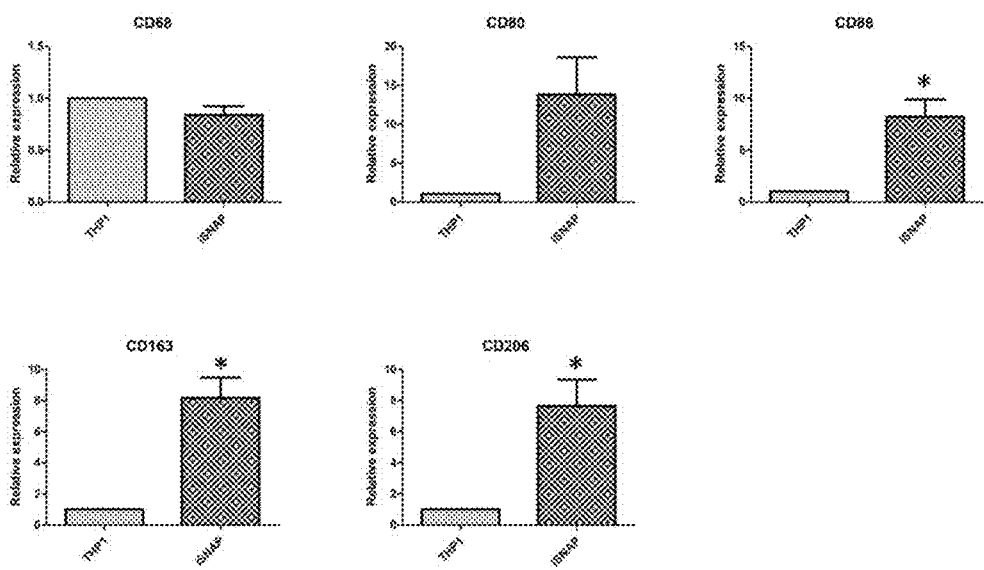
Figure 7:
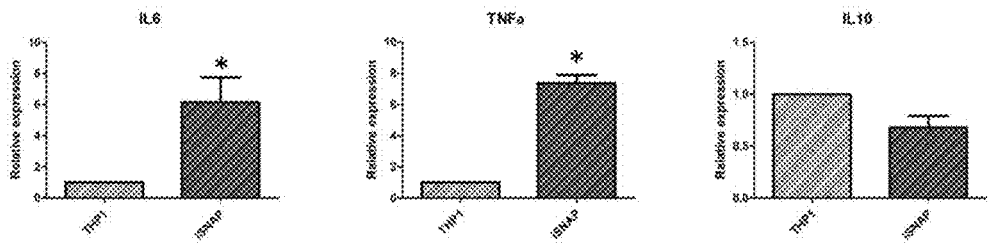

We then examined the molecular profiles of the exemplary iSNAP-engineered THP1 monocytes. The results revealed that the introduced iSNAP can significantly affect the phenotypes of engineered THP1 monocytes (FIG. 7). While iSNAP did not affect the monocyte marker expression CD31, it significantly promoted the expression of CD11b and CD14 macrophage markers (FIG. 7A). Further results indicate that iSNAP expression can induce polarization phenotypes of engineered THP1 monocytes, altering the profiles of M1 and M2 polarization markers, optionally promoting the M1 phenotype (FIG. 7B). The engineered iSNAP THP1 cells also had significantly higher production in pro-inflammatory cytokines (FIG. 7C). Taken together, these results indicate that iSNAP engineering as provided can affect the marker profiles of host THP1 monocytes and specifically promote their inflammatory phenotypes.

Figure 8:
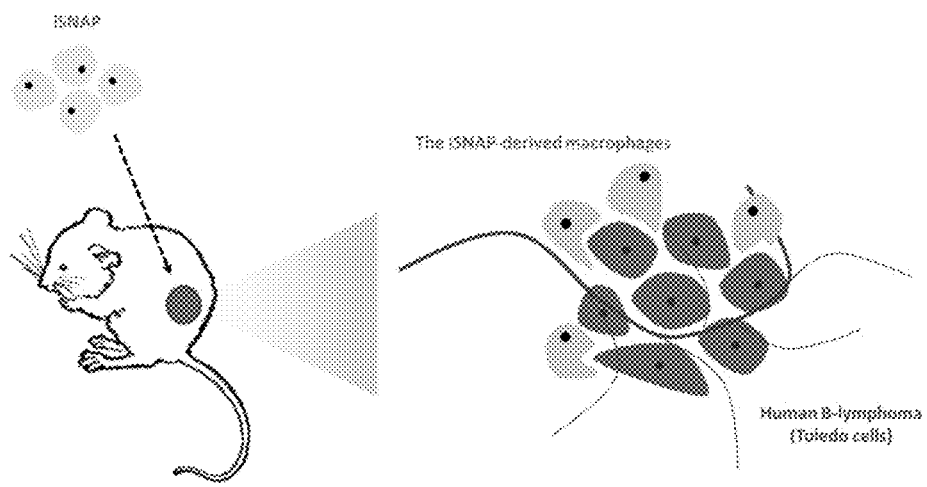
FIG. 8A-B illustrate that exemplary iSNAP-engineered THP1 monocytes as provided herein are better than the naïve THP1 cells in eliminating B-lymphoma (Toledo cells) tumors in mice, guided by the Rituximab recognizing the B-lymphoma Toledo antigen CD20.
Figure 8:
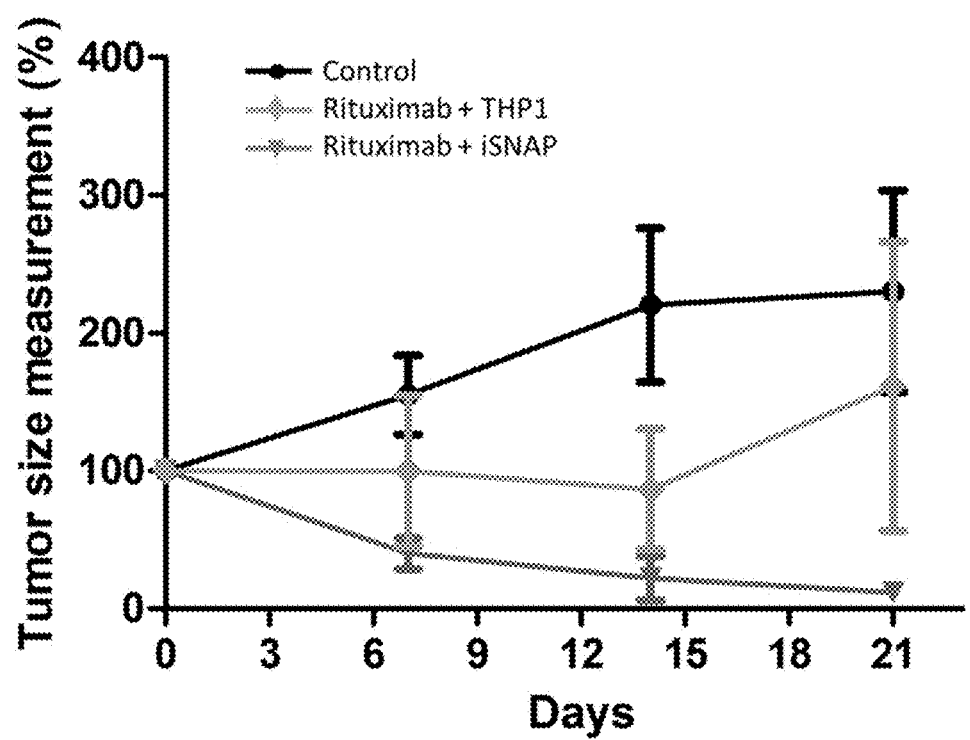

We further examined these engineered THP1 cells in eradicating B-Lymphoma (Toledo) tumors in vivo. Human B-lymphoma tumor model was established by subcutaneous injection of Toledo cells in nude mice (FIG. 8A). The tumors were then treated by local injection of parental control and iSNAP-engineered THP cells, guided by rituximab, an anti-CD20 monoclonal antibody, in recognizing the tumor antigen CD20. The tumor sizes were followed and measured weekly (FIG. 8B). The results showed that the iSNAP-engineered THP1 cells had significantly enhanced capability in eliminating B-lymphoma tumors comparing to parental control THP1 cells, possibly due to their increased inflammatory phenotypes.

In summary, these results demonstrate that iSNAP-engineered monocytes (or macrophages) as provided herein can significantly enhance the immunotherapeutic efficacy of monocytes (and macrophages) in eradicating target cancers or tumors, e.g., as the B-lymphoma tumors used here, in vivo, as demonstrated using a mouse animal model.

Materials and Methods

Reagents and Cell Culture

Fetal bovine serum was obtained from Atlanta Biologicals (Lawrenceville, USA). Rat recombinant platelet-derived growth factor BB (PDGF) and PP1 were from Sigma Aldrich (Milwaukee, USA). Rabbit anti-human RBC antibody (ab34858) was from Abcam (Cambridge, USA). The plasmid encoding the human SIRPα was a generous gift from Dr. Umemori at Department of Biological Chemistry, University of Michigan Medical School. FDA-approved therapeutic antibodies rituximab (anti-CD20, human IgG1) and cetuximab (anti-EGFR, human IgG1) were obtained from Dr. Dahl at VA Medical Center, San Diego. Cell line HEK293T (human embryonic kidney 293T cell line), MEF (mouse embryonic fibroblast), RAW264.7 (mouse macrophage cell line), DLD1 (human colon cancer cell line), Toledo (human non-Hodgkin's B cell lymphoma cell line) and L929 cell line (murine aneuploid fibrosarcoma cell line) were from American Tissue Culture Collection (Manassas, Va.), with the authentication and the verification of the absence of mycoplasma contamination. These cells were cultured in ATCC recommended conditions in a humidified incubator of 95% O2 and 5% $CO_2$ at 37° C.

Human Samples

Normal human peripheral blood samples were obtained from VA San Diego Medical Center, San Diego, Calif. with an IRB-approved protocol (VA San Diego IRB #H150008). Informed consent was obtained from all human participants.

Construction of Plasmids

The Shp2- or Shp1-iSNAP was constructed by fusing DNA sequences encoding

BTAM peptide:
(SEQ ID NO: 1)
GGGGDITYADLNLPKGKKPAPQAAEPNNHTEYASIQTS, derived from ITIM of SIRPα[40], ECFP (Forward primer 1:

forward primer 2:
(SEQ ID NO: 2)
5' CAACCATACCGAATATGCGAGCATTCAGACCAGCGGCGGGTCTGGCGG

GACAAT 3', (SEQ ID NO: 3)
5' CAAAAAACCGGCGCCGCAGGCGGCGGAACCGAACAACCATACCGAATA

TGCGAGC 3', forward primer 3:
(SEQ ID NO: 4)
5' ATATTACCTATGCGGATCTGAACCTGCCGAAAGGCAAAAAACCGGCGC

CGCAGG 3', forward primer 4:
(SEQ ID NO: 5)
5' CGATGGATCCTGGCGGCGGCGGCGATATTACCTATGCGGATCTGAACC

3', reverse primer:
(SEQ ID NO: 6)
5' ACTGCATGCGGCGGCGGTCACGAACTCC 3',

EV linker (116aa)[41]:

forward primer:
(SEQ ID NO: 7)
5' GTACAAGGCATGCGAGCCTGCCAGGGGTACCAG 3', reverse primer:
(SEQ ID NO: 8)
5' GCTTGGTCGACAGGGACATCTGGTCCGGAACC 3', YPet:

forward primer:
(SEQ ID NO: 9)
5' CTAAAGTCGACATGTCTAAAGGTGAAGAATTATTCAC 3', reverse primer:
(SEQ ID NO: 10)
5' ACTGAGCTCCCCGCCTTTGTACAATTCATTCATACCCTCG 3', and the truncated human Shp2 (aa 1-532):

forward primer:
(SEQ ID NO: 11)
5' ACTGAGCTCATGACATCGCGGAGATGGTTTC 3', reverse primer:
(SEQ ID NO: 12)
5' ACTGAATTCTTACTACTCTTCTTCAATCCTGCGCTG 3', or Shp1 (aa 1-525):

```
forward primer:
                                    (SEQ ID NO: 13)
5' ACTGAGCTCATGGTGAGGTGGTTTCACCGAG 3', reverse primer:
                                    (SEQ ID NO: 14)
5' ACTGAATTCTTACTAGACCTCCAGCTTCTTCTTAGTGG 3',
``` in a pcDNA3.1 (Invitrogen) vector using BamHI/EcoRI restriction sites with 6×His tag in front of start codon of the BTAM coding sequence.

The Syk-iSNAPs were constructed by fusing DNA sequences encoding BTAM2 peptide GGYMTLN-PRAPTDDDKNIYLTLPPN (SEQ ID NO:15), including

```
oligonucleotides:
                                    (SEQ ID NO: 16)
5' ATTACCTGGTCCGTCAGGTCTCGGATCCAGGCGGCTACATGACTCTGA

ACCCCAGGGCACCTACTGACGATGATAAAAACATCTACCTGACTCTTCCTC

CCAACGGTACCGGCGGTGAGACCAGCTCACATCACCCGGG 3',
``` derived from ITAM of FcγR IIA, or

```
                                    (SEQ ID NO: 17)
GVYTGLSTRNQETYETLKHE, oligonucleotides:
                                    (SEQ ID NO: 18)
5' GAAGATTACCTGGTCCACGTCAGGTCTCGGATCCAGGTGTTTACACG

GGCCTGAGCACCAGGAACCAGGAGACTTACGAGACTCTGAAGCATGAGGG

TACCGGCGGTGAGACCAGCTCACATCACCCGGGA 3',
``` derived from ITAM of FcRγ, or

```
                                    (SEQ ID NO: 19)
MPDYEPIRKGQRDLYSGLNQR oligonucleotides:
                                    (SEQ ID NO: 20)
5' CGTCAGGTCTCGGATCCACCAGACTATGAGCCCATCCGGAAAGGCCAG

CGGGACCTGTATTCTGGCCTGAATCAGAGAGGCGGGTCTGGCGGGACAGGT

ACCGGCGGTGAGACCAGCTCACATCACCCGGGA 3'
``` derived from ITAM of CD3ε[40],
PCR product of ECFP:

```
forward primer:
                                    (SEQ ID NO: 21)
5' AGATCGGTCTCGGCGGTATGGTGAGCAAGGGCGAGG 3', reverse primer:
                                    (SEQ ID NO: 22)
5' GAGTTCGTGACCGCCGCCCATGcgGAGACCAGCTC 3', EV linker, oligonucleotides:
                                    (SEQ ID NO: 23)
5' CCTGGTCCGTCAGGTCTCCATGCGAGCCTGCCAGGAGCGCAGGCGGAT

CAGCTGGAGGGTCTGCAGGGGGTAGTGCAGGTGGCTCAGCTGGCGGGAGCG

GCTCAGCTGGGGGATCTGCTGGTGGCAGTACCTCAGCAGGCGGTAGCGCCG

GAGGTTCTGCTGGTGGCTCCGCAGGAGGGTCTGCAGGCGGTTCCGGGAGTG

CAGGTGGATCTGCAGGTGGGTCAACAAGTGCTGGTGGATCCGCAGGAGGTT

CAGCAGGCGGGAGTGCTGGAGGCTCTGCAGGCGGTAGCGGGAGTGCCGGTG

GCAGCGCAGGGGGAAGCACTAGTGCTGGAGGCAGTGCAGGTGGCAGCGCAG

GAGGCTCTGCCGGGGGAAGCGCCGGGGGCTCCGGACCAGATGTCCCTGTCG

ACGAGACCAGCTCACATCA 3',
```

PCR product of YPet:

```
forward primer:
                                    (SEQ ID NO: 24)
5' GATCGGTCTCGTCGACTCTAAAGGTGAAGAATTATTCACTG 3', reverse primer:
                                    (SEQ ID NO: 25)
5' AGGGTATGAATGAATTGTACAAAGAGACCAGCTC 3',
``` and PCR product of full length human SYK:

```
forward primer:
                                    (SEQ ID NO: 26)
5' GATCGGTCTCTACAAAGGCGGGGAgctcGCCAGCAGCGGCATGGCTGA

CAGCGCCAACCAC 3', reverse primer:
                                    (SEQ ID NO: 27)
5' CAATTACTACTATGACGTGGTGAACTAAGAATTCGAGACGAGCTC

3',
``` into BamHI/EcoRI restriction sites of pcDNA3.1 vector using Golden Gate assembly, respectively.

FF mutant of Syk-iSNAP was constructed by replacing oligonucleotides coding wild type peptide with

```
oligonucleotides:
                                    (SEQ ID NO: 28)
5' ATTACCTGGTCCGTCAGGTCTCGGATCCAGGCGGCTTTATGACTCTG

AACCCCAGGGCACCTACTGACGATGATAAAAACATCTTTCTGACTCTTCC

TCCCAACGGTACCGGCGGTGAGACCAGCTCACATCACCCGGG 3'
``` carrying Y to F mutations.

For the SIRPα fused iSNAPs, the PCR product of gene sequence encoding human SIRPα (aa 1-425):

```
forward primer:
                                    (SEQ ID NO: 29)
5' AGCCCAAGCTTGCCACCATGGAGCCCGCC 3', reverse primer:
                                    (SEQ ID NO: 30)
5' TCGGGGATCCGAATTTGTGTCCTGTGTTATTTC 3',
``` was inserted in 5' of iSNAP coding sequences using HindIII/BamHI restriction sites. Deletion and point mutations of iSNAP were generated using QuikChange Site- Directed Mutagenesis Kit™ (Agilent Technologies), with primer sets:

(SEQ ID NO: 31)
5' CAGGAGTGCAAACTTCTCTACAGCCAGCGCAGGATTGAAGAAGAG 3',
and (SEQ ID NO: 32)
5' CTCTTCTTCAATCCTGCGCTGGCTGTAGAGAAGTTTGCACTCCTG 3', for SIRPα Shp2-iSNAP ΔPTP:
and;

(SEQ ID NO: 33)
5' GTGAAAACCGTGGCTGTGAGGATACTGAAAAACGAGGCCA 3',
and (SEQ ID NO: 34)
5' TGGCCTCGTTTTTCAGTATCCTCACAGCCACGGTTTTCAC 3', for SIRPα Syk-iSNAP K402R.

For SIRPα-YPet and SIRPα-no ITIM, PCR products of human SIRPα coding sequence:

forward primer:
(SEQ ID NO: 35)
5' AGCCCAAGCTTGCCACCATGGAGCCCGCC 3', reverse primer:
(SEQ ID NO: 36)
5' CGTGGAATTCTGTTCCGCCAGATCCGCCCTTCCTCGGGACCTG 3' for aa 1-504, full length; or, reverse primer:
(SEQ ID NO: 37)
5' CGTGGAATTCTGTTCCGCCAGATCCGCCATTTGTGTCCTGTGTTATTT C 3', for aa 1-425, no ITIM), and PCR product of YPet:

forward primer:
(SEQ ID NO: 38)
5' TCCGGAATTCATGTCTAAAGGTGAAGAATTATTCACTG 3', reverse primer:
(SEQ ID NO: 39)
5' ACAGACCTCGAGTCATTTGTACAATTCATTCATACCCT 3', were inserted into HindIII/Xho I restriction sites of pcDNA3.1.

ECEPT65A/W66A and YPet Y66A mutations were done with primer sets:

(SEQ ID NO: 40)
5' CGTGACCACCCTGGCCGCGGGCGTGCAGTGC 3',
and (SEQ ID NO: 41)
5' GCACTGCACGCCCGCGGCCAGGGTGGTCACG 3';

(SEQ ID NO: 42)
5' TGGCCAACCTTAGTCACTACTTTAGGTGCTGGTGTTCAATGTTTTG 3',
and (SEQ ID NO: 43)
5' CAAAACATTGAACACCAGCACCTAAAGTAGTGACTAAGGTTGGCCA 3', respectively.

The constructed plasmids were confirmed by restriction enzyme digestion and DNA sequencing.

Protein Expression and Purification

HEK cells transfected with wild type iSNAPs or their mutants were washed with cold PBS and then lysed in buffer containing 50 mM Tris-HCl pH 7.5, 100 mM NaCl, 1 mM EDTA, 0.2 mM PMSF, 0.2% Triton X-100 and a protease inhibitor cocktail tablet (Roche). Lysates were centrifuged at 10,000×g at 4° C. for 10 min. Supernatants were incubated with Ni-NTA agarose (Qiagen) to capture the desired protein products via their 6-His tag at the N-termini, which were then washed with 50 mM Tris-HCl pH 7.5, 100 mM NaCl, 10 mM imidazole. iSNAP proteins were eluted in a buffer containing 50 mM Tris-HCl pH 7.5, 100 mM NaCl, and 100 mM imidazole.

In Vitro Kinase Assays

Purified proteins were dialyzed overnight at 4° C. in kinase buffer (50 mM Tris-HCl pH 8.0, 100 mM NaCl, 10 mM $MgCl_2$, and 2 mM dithiothreitol). Fluorescence emission spectra of the purified iSNAP proteins (50 nM) were measured in 96-well plates with an excitation wavelength of 430 nm using a fluorescence plate reader (TECAN, Sapphire II). To detect FRET changes of the iSNAPs, emission ratios of acceptor/donor (526 nm/478 nm) were measured at 30° C. before and after the addition of 1 mM ATP and 100 nM active recombinant Src (Millipore).

In Vitro Phosphatase Activity Assays

After kinase assay, phosphatase activity was measured by adding fluorogenic 6,8-difluoro-4-methylumbelliferyl phosphate (DiFMUP; Invitrogen) as the substrate. In brief, each reaction contained 50 mM Tris pH 8, 100 mM NaCl, 10 mM $MgCl_2$, 2 mM dithiothreitol, 100 nM Src kinase, 50 nM iSNAP proteins and 50 μM DiFMUP in a total reaction volume of 100 μl in a well of 96-well plates. Reactions were initiated by the addition of DiFMUP, followed by measuring the fluorescence signal of the reaction product, 6,8-difluoro-4-methylumbelliferone, at an excitation wavelength of 355 nm and an emission of 460 nm with a plate reader (TECAN, Sapphire II). The intensity slope of the fluorescent product over time was calculated and compared. Our statistics were performed with two-tailed Student t-test.

Immunoblotting

After in vitro assays, the iSNAP proteins were resolved by SDS-PAGE. The proteins were then transferred onto a nitrocellulose membrane and blocked with 5% bovine serum albumin in TTBS buffer (50 mM Tris-HCl, 145 mM NaCl, 0.05% Tween-20, pH 7.4) for 2 hours (hr) at room temperature (RT). Membranes were further incubated with primary antibodies overnight at 4° C., washed and then incubated with HRP-conjugated secondary antibodies for 2 hr at RT. Signals were detected using SuperSignal™ Western Pico or Femto ECL Kit™ (Pierce). Monoclonal anti-phosphotyrosine pY20 antibody was from BD Transduction laboratory (61000, 1:1000 dilution). And polyclonal anti-GFP antibodies (sc-8334, 1:1000 dilution) as well as HRP-conjugated secondary antibodies (sc-2004, sc-2005, 1:2000 dilution) were purchased from Santa Cruz Biotechnology.

Microscopy, Image Acquisition and Analysis

Glass-bottom dishes (Cell E&G Inc.) were coated with 10 µg ml^-1 fibronectin (Sigma) overnight at 37° C. Transfected or electroporated cells were plated onto these dishes overnight in medium containing 0.5% FBS before imaging. During imaging, cells were maintained in medium containing 0.5% FBS with 5% CO2 supplement at 37° C. and a few frames of images were acquired to obtain the basal level before adding stimulation. For PDGF stimulation, PDGF was added into medium to reach final concentration 10 ng ml^-1. For RBCs, Toledo and DLD1 cells stimulation, those cells were washed with PBS plus 0.4% BSA, and opsonized with rabbit anti-human RBC IgG (Abcam, ab34858, 5 µg ml^-1), rituximab (anti-CD20 mAb, 10 µg ml^-1), cetuximab (anti-EGFR mAb, 2 µg ml^-1) or trastuzumab (anti-HER2 mAb, 2 µg ml^-1) for 60 min at RT, respectively. After washing with PBS plus 0.4% BSA, cells were re-suspended in medium with 0.5% FBS and applied into dishes. Images were obtained by a Nikon™ eclipse Ti inverted microscope equipped with a cooled charge-coupled device camera (Cascade 512B; Photometrics) with 512×512 resolution using MetaFluor 6.2™ software (Universal Imaging). The following filter sets (Chroma) were used in our experiments for FRET imaging: a dichroic mirror (450 nm), an excitation filter 420/20 nm, an ECFP emission filter 475/40 nm, and a FRET emission filter 535/25 nm. The excitation filter for ECFP at 420±20 nm was specifically selected to shift toward lower wavelength away from the peak excitation spectrum of ECFP to reduce the cross-excitation of the FRET acceptor YPet, which has significantly higher brightness than ECFP. This filter selection can minimize the effect of bleed-through on the FRET channel. The fluorescence intensity of non-transfected cells was quantified as the background signal and subtracted from the ECFP and FRET signals of transfected cells. The pixel-by-pixel ratio images of FRET/ECFP were calculated based on the background-subtracted fluorescence intensity images of ECFP and FRET. These ratio images were displayed in the intensity modified display (IMD) mode in which the color and brightness of each pixel is determined by the FRET/ECFP ratio and ECFP intensity, respectively. The emission ratios were quantified by MetaFluor™ software and our statistics were performed with two-tailed Student t-test using Excel™ (Microsoft).

Recombinant Human CD47 Production and Coating on Beads

Plasmid encoding the extracellular domain of human CD47 was a gift from Dr. Dennis E. Discher (Molecular and Cell Biophysics Laboratory, University of Pennsylvania). The plasmid was transfected into HEK293T cell using Lipofectamine 2000 (Invitrogen). After 36 hr culture, medium containing secreted CD47-CD4d3 was concentrated using a 10K MWCO Amicon™ (Millipore), and CD47-CD4d3 was biotinylated at the C terminus using a biotin-protein ligase (Avidity, LLC) and dialyzed against PBS for 24 hr. The biotinylated CD47-CD4d3 was affinity purified using monomeric avidin (Promega) and dialyzed against PBS for 24 hr. Streptavidin-coated polystyrene beads of 4 µm diameter (Spherotech) were washed in PBS plus 0.4% BSA, and then incubated with biotinylated CD47 at RT for 30 min, followed by 3× wash and re-suspension in cell culture medium with 0.5% FBS. For IgG coating, streptavidin-coated polystyrene beads were incubated with rabbit anti-streptavidin IgG (Abcam, ab6676, 1:3000 dilution) at RT for 30 min.

Flow Cytometry

For soluble CD47 binding assay, HEK293T cells were transfected with SIRPα Shp2-iSNAP, its mutants, SIRPα-YPet, or truncated SIRPα (no ITIM motif) fused to YPet™ by Lipofectamine 2000™ (Life technologies). After 36 hr culture, transfected HEK293T cells were detached by treatment of 10 mM EDTA and non-specific surface residues were blocked for 10 min by PBS plus 0.4% BSA. Cells were then incubated with biotinylated CD47 at room temperature (RT) for 30 min, washed and then incubated with PE conjugated streptavidin (Life technologies, SA10041™, 1:1000 dilution) at RT for 30 min.

For the measurement of surface CD47, CD20 and EGFR expressions, RBCs, Toledo and DLD1 (detached by treatment of Accutase™, Innovative Cell Technologies, Inc.) cells were washed with PBS plus 0.4% BSA, and incubated with mouse anti-human CD47 IgG (Abcam, ab3283, 1:1000 dilution), rituximab (1:1000 dilution), or cetuximab (1:1000 dilution) at RT for 60 min, respectively. After wash with PBS plus 0.4% BSA, cells were incubated with secondary antibodies: Alexa Fluor 488-conjugated goat anti-mouse antibody for CD47, (Life technologies, A32723, 1:1000 dilution), PE-conjugated rabbit anti-human antibody (Abcam, ab98596, 1:500 dilution) for CD20 and EGFR, at RT for 60 min.

For RBC opsonization, RBCs were washed with PBS plus 0.4% BSA, incubated with rabbit anti-hRBC IgG (5 µg ml^-1) for 60 min at RT, followed by washing and incubation with Alexa Fluor 594-conjugated goat anti-rabbit secondary antibody (Life technologies, R37117, 1:1000 dilution) at RT for 60 min.

Cells were analyzed using flow cytometry after antibody staining. The acquisition configurations using a BD Accuri™ C6 (BD Immunocytometry Systems) for different fluorescent proteins and dyes are listed as following: YPet (Ex:488, Em:530/30 nm); PE (Ex:488, Em:575/26 nm); Deep red dyes (Ex:640, Em:660/20 nm).

Differentiation of Bone Marrow Derived Macrophages

Bone marrow from wild-type C57BL/6 12-20 weeks female mice were harvested from freshly isolated femurs, tibiae, and humeri (5000227M, UCSD Animal Care Program/IACUC). After removal of connective tissues and muscles, bone marrow cells were flushed out and single cell suspensions were made by pipetting and passing bone marrow through a sterile 70-µm filter (BD Falcon). Remaining RBCs were lysed by ACK buffer (0.15M NH$_4$Cl, 10 mM KHCO$_3$, 0.1 mM EDTA). Macrophages were differentiated by incubating bone marrow cells for 7 days with complete RPMI 1640, supplemented with 10% L929-conditioned medium (containing M-CSF). Macrophages were harvested after 15-minute incubation with 10 mM EDTA.

Electroporation of Macrophages and Phagocytosis Assay iSNAPs were introduced into RAW 264.7 macrophages and BMDMs by electroporation. Briefly, 4×10$^6$ RAW 264.7 or BMDMs were re-suspended in 240 µl of RPMI 1640 with 20 µg plasmids, and then electroporated (250V, 950 mF, ∞Ω). For phagocytosis assays, transfected macrophages were plated in 35 mm dishes at 20% confluency. RBCs, Toledo and DLD1 (detached by treatment of Accutase) cells were washed 3 times with PBS, and incubated with Cell-Tracker™ Deep Red dye (Life technologies) in PBS (1 µM for RBCs labeling, 0.3 µM for Toledo and DLD1 cells labeling) for 30 min at RT followed by 3 times of wash with PBS. RBCs were added to RAW264.7 macrophages at a ratio of 10:1 and allowed to incubate at 37° C. for 30 min in the presence of rabbit anti-hRBC IgG (5 µg ml^-1). Free RBCs were removed by washing with PBS plus 0.4% BSA; bounded RBCs were lysed by adding ACK buffer (NH$_4$Cl 31 mM, KHCO$_3$ 2 mM, EDTA 20 µM) for 2 min. Toledo or DLD1 cells were added to BMDMs at a ratio of 10:1 and allowed to incubate at 37° C. for 4 hrs in the presence of rituximab (10 µg ml^-1) for Toledo cells or cetuximab (2 µg ml^-1) for DLD1 cells, respectively. Free Toledo or DLD1 cells were removed by washing with PBS; bounded cells were dissociated by incubation with EDTA 10 mM at 37° C. for 20 min and dissociation efficiency was confirmed under microscope[42,43]. Macrophages were detached by scratching with plastic lifter and kept in suspension. Engineered macrophage population defined as YPet+ cells were measured by flow cytometry and gated, and the signal of ingested cells (Deep Red+, Ex:640 nm, Em:660/20 nm) was determined within engineered macrophage population. Expression level of SIRPα Shp2-iSNAP or control constructs represented by the intensity of YPet signal (Ex: 488 nm, Em: 575/26 nm) were recorded simultaneously. Doublets discrimination flow cytometry was used to further distinguish internalized from externally bound tumor cells. The phagocytic potential (mean±s.e.m. from 6-8 measurements) of different macrophage groups were normalized to the level of phagocytosis of target cells by macrophages expressing SIRPα-YPet. Each dot represents mean normalized phagocytic rate from an individual experiment, error bars represent s.e.m.

Statistical Analysis

Statistical analysis was performed by two-sided Mann-Whitney U test in MATLAB, with the p-values adjusted for comparison of multiple groups. Statistics of FIG. 1d was done by exact randomized permutation test. All the center values are mean±s.e.m. A significant difference was determined by P value <0.05. All the experiments were replicated at least 3 times and represented biological replicates.

Data availability statement. The DNA sequences of iSNAP have been deposited into NCBI GenBank (Shp2-iSNAP: MF434748, SIRPα Shp2-iSNAP: MF434749, SIRPα Shp2-iSNAP APTP: MF434750, SIRPα Syk-iSNAP: MF434751, SIRPα YPet: W434752, SIRPα no ITIM YPet: W434753). The data that support the findings of this study are available from the corresponding author upon request.

A number of embodiments of the invention have been described. Nevertheless, it can be understood that various modifications may be made without departing from the spirit and scope of the invention. Accordingly, other embodiments are within the scope of the following claims.

What is claimed is:

1. A Src homology region 2 domain-containing phosphatase-2 (Shp2)-actuating protein (iSNAP) (Shp2-iSNAP) chimeric protein comprising in either: amino terminal to carboxy terminal order, or carboxy terminal to amino terminal order, modules comprising:
   (a) a bi-phosphorylatable peptide comprising a bisphosphoryl tyrosine-based activation (BTAM) motif,
   (b) a Fluorescent Protein (FP) Förster Resonance Energy Transfer (FRET) (FP FRET) pair comprising an enhanced cyan fluorescent protein (ECFP) motif and a YPet fluorochrome,
   (c) a truncated Shp2 domain consisting of an N-Src Homology 2 (N-SH2) domain and a C-Src Homology 2 (C-SH2) domain,
   wherein an unphosphorylated Shp2 domain binds or quenches the PTP domain or the kinase domain; and,
   (d) a phosphatase (PTP) domain or a kinase domain,
   and when the bi-phosphorylatable peptide, when phosphorylated, binds the N-SH2 domain and the C-SH2 domain and liberates or unquenches or activates the PTP domain or the kinase domain, and unquenching or activating of the PTP domain or the kinase domain causes or results in the emission of a detectable signal by the YPet fluorochrome.

2. The Shp2-iSNAP chimeric protein of claim 1 further comprising a transmembrane domain.

3. A recombinant nucleic acid encoding the Shp2-iSNAP chimeric protein of claim 1.

4. An expression vehicle or cassette, a vector, a virus, or a plasmid comprising or having contained therein the nucleic acid of claim 3.

5. An engineered cell comprising or having contained therein the nucleic acid of claim 3.

6. An engineered eukaryotic cell comprising or expressing the Shp2-iSNAP chimeric protein of claim 1.

7. A kit comprising an engineered eukaryotic cell of claim 5.

8. A product or article of manufacture comprising an engineered cell, or eukaryotic cell, of claim 5.

9. The Shp2-iSNAP chimeric protein of claim 1, wherein the kinase comprises a tyrosine kinase (Syk).

10. The Shp2-iSNAP chimeric protein of claim 1, wherein when the YPet fluorochrome comes into physical proximity to the enhanced cyan fluorescent protein (ECFP) motif, the physical proximity causes the YPet fluorochrome to emit a 535 nm signal.

11. The Shp2-iSNAP chimeric protein of claim 2, wherein the Shp2-iSNAP chimeric protein further comprises an extracellular domain capable of binding to a ligand.

12. The Shp2-iSNAP chimeric protein of claim 2, wherein the Shp2-iSNAP chimeric protein further comprises a transmembrane domain and an extracellular domain capable of binding to a ligand.

13. The expression vehicle or cassette, vector, virus, or plasmid of claim 4, wherein the virus is or is derived from a lentivirus, a poliovirus, or an adenovirus.

14. The engineered cell of claim 5, wherein the cell is a bacterial cell, a yeast cell, a mammalian cell or a human cell, and or the cell is a macrophage, a microglial cell, an osteoclast, a Kupffer cell or a monocyte.

15. The Shp2-iSNAP chimeric protein of claim 2, wherein the transmembrane domain is joined or fused to the bi-phosphorylatable peptide or BTAM motif.

16. The Shp2-iSNAP chimeric protein of claim 2, wherein when the extracellular domain binds to its ligand the bi-phosphorylatable peptide or BTAM motif is biphosphorylated, and when bi-phosphorylated, the bi-phosphorylated peptide or BTAM motif binds the truncated N-SH2 domain and the C-SH2 domain and liberates or unquenches or the PTP domain or the kinase domain, and the unquenching or activating of the PTP domain or the kinase domain causes emission of a detectable signal by the YPet fluorochrome, wherein when the YPet fluorochrome comes into physical proximity to the enhanced cyan fluorescent protein (ECFP) motif it emits a 535 nm signal.

17. The Shp2-iSNAP chimeric protein of claim 2, wherein the extracellular domain capable of binding to a ligand comprises a Signal Regulatory Protein α(SIRPα) domain and the ligand comprises a Cluster of Differentiation 47 (CD47) protein, a CD47-coated particle or a CD47-expressing liposome or cell.

18. The Shp2-iSNAP chimeric protein of claim 17, wherein the SIRPα domain comprises a human SIRPα domain.

19. The engineered eukaryotic cell of claim 6, wherein the cell is: a mammalian cell, or an immune cell.

20. The engineered eukaryotic cell of claim 6, wherein the cell is a human cell.

21. The engineered eukaryotic cell of claim 19, wherein the immune cell is a macrophage, monocyte, microglial cell, osteoclast, Kupffer cell or dendritic cell is a human macrophage, microglial cell, osteoclast, Kupffer cell monocyte or dendritic cell.

22. The kit comprising of claim 7, wherein the kit further comprises: an antibody or mAb capable of specifically binding to the cancer cell, tumor or dysfunctional cell.

23. The product or article of manufacture of claim 8, wherein the product of manufacture is: a device; an implant; a vial, a carpule or storage container; or a catheter.

* * * * *